(12) United States Patent
Medof et al.

(10) Patent No.: US 11,130,801 B2
(45) Date of Patent: Sep. 28, 2021

(54) METHOD FOR INHIBITING PLATELET DERIVED GROWTH FACTOR SIGNALING WITH C3AR OR C5AR ANTIBODIES

(75) Inventors: M. Edward Medof, Pepper Pike, OH (US); Michael G. Strainic, Westlake, OH (US); Elliot Pohlmann, Roanoke, VA (US); Ming-Shih Hwang, Danbury, CT (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 13/350,402

(22) Filed: Jan. 13, 2012

(65) Prior Publication Data
US 2012/0315279 A1    Dec. 13, 2012

Related U.S. Application Data

(60) Provisional application No. 61/432,498, filed on Jan. 13, 2011.

(51) Int. Cl.
| | |
|---|---|
| *C07K 16/18* | (2006.01) |
| *C07K 16/28* | (2006.01) |
| *A61K 39/00* | (2006.01) |
| *C07K 16/24* | (2006.01) |
| *G01N 33/564* | (2006.01) |
| *A61K 45/06* | (2006.01) |
| *A61K 38/58* | (2006.01) |
| *A61K 38/08* | (2019.01) |
| *A61K 38/06* | (2006.01) |
| *A61K 38/57* | (2006.01) |

(52) U.S. Cl.
CPC .............. *C07K 16/18* (2013.01); *A61K 38/06* (2013.01); *A61K 38/08* (2013.01); *A61K 38/57* (2013.01); *A61K 38/58* (2013.01); *A61K 45/06* (2013.01); *C07K 16/248* (2013.01); *C07K 16/28* (2013.01); *G01N 33/564* (2013.01); *A61K 2039/507* (2013.01); *C07K 2317/32* (2013.01); *C07K 2317/73* (2013.01); *C07K 2317/76* (2013.01); *G01N 2500/10* (2013.01)

(58) Field of Classification Search
CPC .............. C07K 16/40; C07K 16/2896; C07K 2317/76; C07K 14/472; C07K 16/28; C07K 2317/734; C07K 16/2863; A61K 38/00; A61K 2039/505; A61K 2039/507; A61B 5/412; A61B 5/418
See application file for complete search history.

(56) References Cited

U.S. PATENT DOCUMENTS 7,816,497 B2 * 10/2010 Ambati .................. 530/387.9
2008/0214436 A1 * 9/2008 Yu et al. .................. 514/2

FOREIGN PATENT DOCUMENTS

| WO | WO2008009062 | * | 1/2008 | ............. A61K 38/12 |
| WO | WO2008022390 | * | 2/2008 | ............. C07K 16/28 |

OTHER PUBLICATIONS

Cortright et al. C5a, but not C3a, increases VEGF secretion in ARPE-19 human retinal pigment epithelial cells. Current Eye Research, 34, 57-61, 2009.*
Girardi G., Guilty as Charged: All available evidence implicates complement's role in fetal demise. Am. J. Reprod. Immun. 59, 183-192, 2008.*
Lee et al., Human C5aR knock-in mice facilitate the production and assessment of anti-inflammatory monoclonal antibodies. Nat. Biotech., 24, 1279-1284, 2006.*
Sakuma et al., The intrinsic complement regulator decay-accelerating factor modulates the biological response to vascular injury. Arterioscler. Thromb. Vasc. Biol., 1196-1202, 2010.*
Klos et al., The role of the anaphylatoxins in health and disease. Mol. Immunol., 46, 2753-2766, 2009.*
Kildsgaard et al., Cutting Edge: Targeted disruption of the C3a receptor gene demonstrates a novel protective anti-inflammatory role for C3a in endotoxin-shock. J. Immunol., 165, 5406-5409, 2000.*
Zwirner et al., Expression of anaphylatoxin C5a receptor in non-myeloid cells. Mol. Immunol., 36, 877-884, 1999.*
Monk et al., Function, structure and therapeutic potential of complement C5a receptors. Brit. J. Pharmacol. 152, 429-448, 2007.*
Woodruff et al., Inhibiting the C5-C5a receptor axis, Mol. Immunol., 48, 1631-1642, 2011.*
Agrawal et al., Molecular targets and regulators of cardiac hypertrophy. Pharmacol. Res. 61, 269-280, 2010.*
Sano et al., Impact of Stat3 activation upon skin biology: A dichotomy of its role between homeostasis and diseases. J. Dermatol. Sci., 50, 1-14, 2008.*
Klein et al., Survival and proliferation factors of normal and malignant plasma cells. Int. J. Hematol., 78, 106-113, 2003.*
Wertz K., Lycopene Effects Contributing to Prostate Health. Nutrit.& Cancer, 61, 775-783, 2009.*
Wetsel et al., Complement Anaphylatoxins (C3a, C4a, C5a) and Their Receptors (C3aR, C5aR/CD88) as Therapeutic Targets in Inflammation. Chapter 5, pp. 113-153, 2000, in Contemporary Immunology: Therapeutic Interventions in the Complement System. Edited by: J. O. Lambris and V. M. Holers, Humana Press Inc., Totowa, NJ. ISSN/ISBN: 9781468496123.*
Sakuma et al. The intrinsic complement regulator Decay-Accelerating Factor modulates the biological response to vascular injury. Arterioscler. Thromb. Vase. Biol. 30, 1196-1202, 2010.*
Wetsel et al., Complement anaphylatoxins (C3a, C4a, C5a) and their receptors (C3aR, C5aR/CD88) as therapeutic targets in inflammation. In: Therapeutic interventions in the complement system, p. 113-153, 2000. Editor(s): Lambris, John D.; Holers, V. Michael. Humana Press Inc.:Totowa, N. J.*

(Continued)

Primary Examiner — Elly-Gerald Stoica
(74) Attorney, Agent, or Firm — Tarolli, Sundheim, Covell & Tummino LLP

(57) ABSTRACT

A method of modulating growth factor responses of cells expressing C3a receptor (C3aR) and C5a receptor (C5aR) and at least one growth factor receptor includes administering to the cells at least one agent that modulates C3aR and/or C5aR signaling of the cells.

7 Claims, 18 Drawing Sheets

(56) References Cited

OTHER PUBLICATIONS

C5aR and C3aR Antagonist, web searched on MERCK website (https://www.sigmaaldrich.com/catalog/) on Apr. 27, 2020. (Year: 2020).*
Anti-C3aR antibody sc-53782 (www.scbt.com) on Apr. 27, 2020. (Year: 2020).*
Anti-C3aR antibody sc-53785 (www.scbt.com) on Apr. 27, 2020. (Year: 2020).*
Anti-C5aR antibody sc-53788 (www.scbt.com) on Apr. 27, 2020. (Year: 2020).*
Anti-C5aR antibody sc-53793 (www.scbt.com) on Apr. 27, 2020. (Year: 2020).*
Anti-C5aR antibody sc-53794 (www.scbt.com) on Apr. 27, 2020. (Year: 2020).*
Anti-C5aR antibody sc-53795 (www.scbt.com) on Apr. 27, 2020. (Year: 2020).*
Anti-C5aR antibody sc-53796 (www.scbt.com) on Apr. 27, 2020. (Year: 2020).*
Anti-C5aR antibody sc-53797 (www.scbt.com) on Apr. 27, 2020. (Year: 2020).*
Anti-C5aR antibody sc-70813 (www.scbt.com) on Apr. 27, 2020. (Year: 2020).*
Anti-C5aR antibody sc-133172 (www.scbt.com) on Apr. 27, 2020. (Year: 2020).*
Anti-C5aR antibody sc-271949 (www.scbt.com) on Apr. 27, 2020. (Year: 2020).*

* cited by examiner

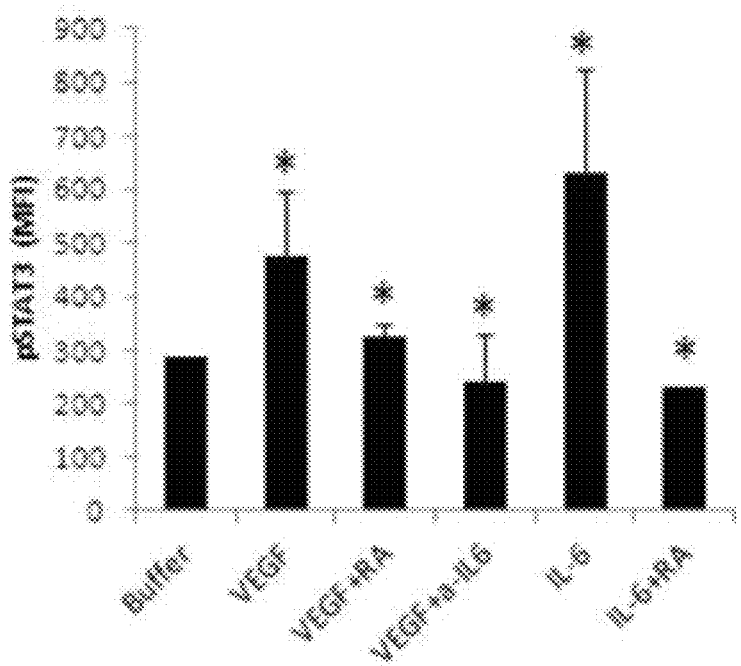
Fig. 29
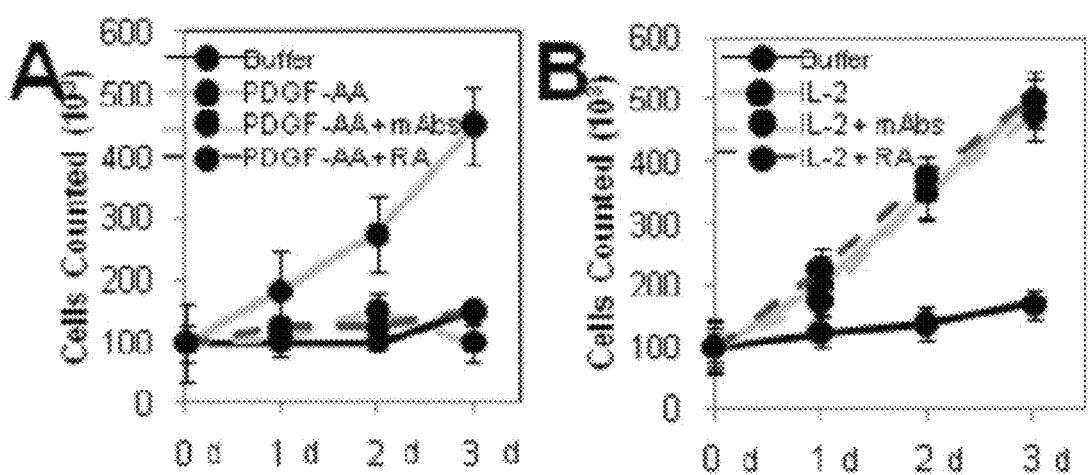
Figs. 30A-B

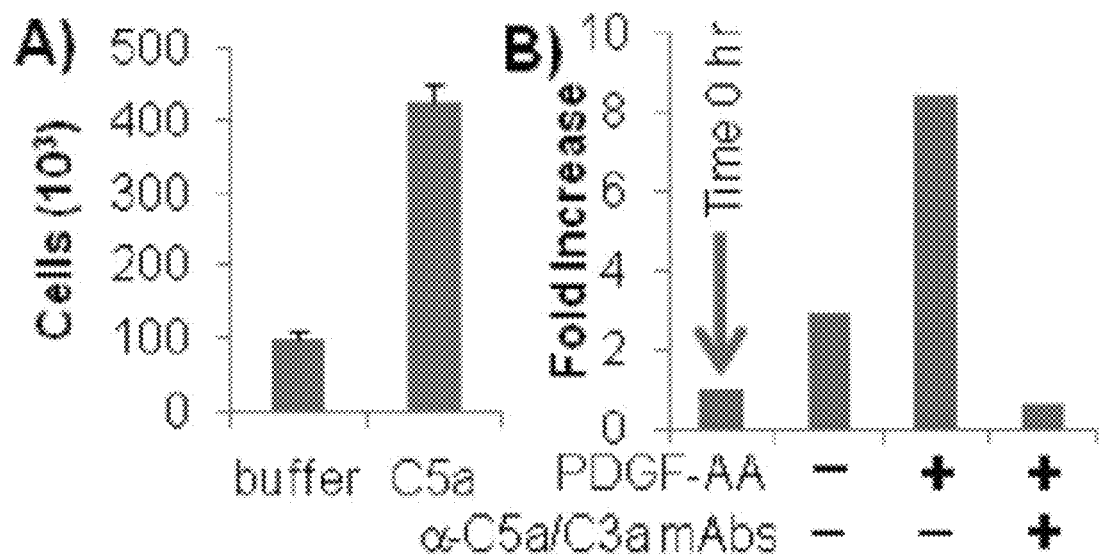
Figs. 31A-B
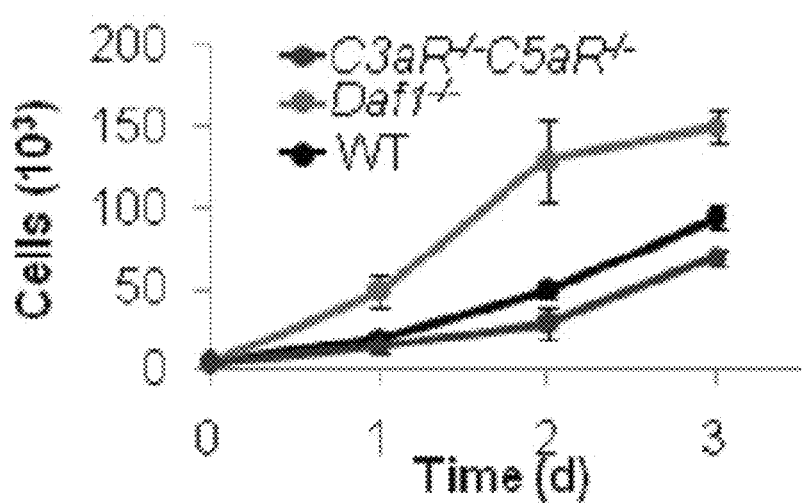
Fig. 32

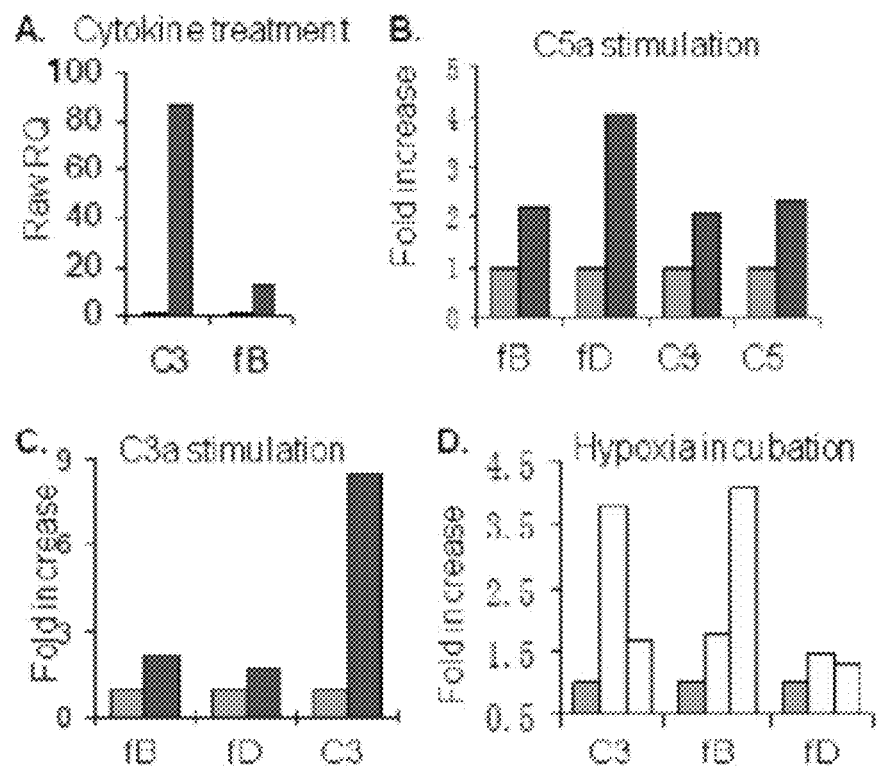
Figs. 33A-D
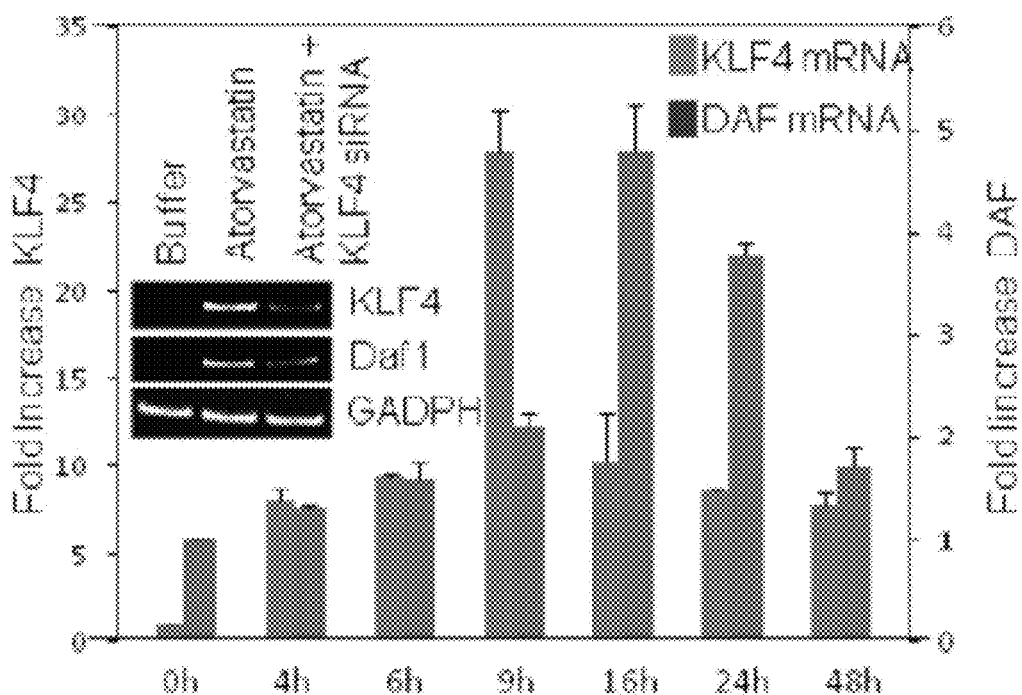
Fig. 34

METHOD FOR INHIBITING PLATELET DERIVED GROWTH FACTOR SIGNALING WITH C3AR OR C5AR ANTIBODIES

RELATED APPLICATION

This application claims priority from U.S. Provisional Application No. 61/432,498, filed Jan. 13, 2011, the subject matter, which is incorporated herein by reference in its entirety.

This invention was made with government support under Grant No. AI023598 awarded by The National Institutes of Health, and W81XWH-09-1-0074, awarded by the Department of Defense. The United States government has certain rights in the invention.

TECHNICAL FIELD

This application relates to a compositions and methods of modulating growth factor function and to compositions and methods of treating growth factor mediated disorders and conditions.

BACKGROUND

The complement system is made up of several distinct plasma proteins that react with one another to opsonize pathogens and induce a series of inflammatory responses that help combat infection. The complement cascade can be activated on the surface of a pathogen through one or more of the three distinct pathways, the classical, the MB-Lectin, and the alternative. Each of these three pathways follows a sequence of reactions to generate proteases known as C3 convertases. These active proteases, bound covalently to the pathogen surface, are responsible for the cleavage of complement component C3 for the generation of large amounts of C3b, the main effector molecule of the complement system, and C3a, a peptide mediator of inflammation. The C3b molecules bind covalently to the pathogen, acting as opsonins, and target it for destruction by phagocytes prepared with receptors for C3b. The C3b also binds with C3 convertase to form C5 convertase, responsible for producing a second peptide mediator of inflammation, C5a, as well as C5b, initiator of the later events of complement activation.

Virtually all aspects of development, growth, cellular homeostasis, and tissue regeneration/repair are regulated by growth factors. As examples, angiogenesis depends on VEGF, epithelial cell growth on EGF, smooth muscle cell growth on PDGF, monocyte/macrophage growth on GM-CSF, and nerve growth on NGF. Each of these growth factors mediates its effects via ligation of specific receptor tyrosine kinases (RTKs). Under homeostatic conditions, tonic growth factor production and RTK signaling confers survival signals. In response to exogenous stimuli, e.g., hypoxia in the case of VEGF, amplified growth factor production and potentiated RTK signaling triggers the cell cycle and thereby induces proliferation. According to current concepts, RTK auto-phosphorylation resulting from engagement of its respective growth factor initiates downstream signaling cascades that confer its viability and mitotic effects directly.

Studies involving VEGF and its connection with components C3a and C5a have been shown to have clinical significance as well. Age-related macular degeneration (AMD) is the leading cause of permanent vision loss among the elderly in many industrialized countries. In a study conducted with retinal pigmented epithelium (RPE) cells, bioactive fragments of C3a and C5a were shown to be present in drusen of patients with AMD, and that C3a and C5a induce VEGF expression. Furthermore, these components were shown to be generated early in the course of laser-induced choroidal neovascularization (CNV), an accelerated model of neovascular AMD driven by VEGF and recruitment of leukocytes into the choroid.

SUMMARY

This application relates to a method of modulating growth factor responses of cells expressing C3a receptor (C3aR) and C5a receptor (C5aR) and at least one growth factor receptor. The method includes administering to the cells at least one agent that modulates C3aR and/or C5aR signaling of the cells.

In some embodiments, the agent can inhibit C3aR and/or C5aR signaling of the cells and be administered to the cells at an amount effective to inhibit at least one of growth, viability, or mitosis of the cells. The agent that inhibits C3aR and/or C5aR signaling of the cells can be selected from the group consisting of a complement antagonist that substantially reduces the interaction of at least one of C3a or C5a with the C3a receptor (C3aR) and C5a receptor (C5aR), a STATS/IL-6 signaling pathway antagonist (e.g., a STATS inhibitor and an IL-6 inhibitor), a thrombin inhibitor, and a combination thereof.

In some embodiments, the cells can include at least one of smooth muscle cells, endothelial cells, leukocytes, cancer cells, neural cells, or fibroblasts. The agent can inhibit at least one of growth, viability, or mitosis of the smooth muscle cells, endothelial cells, leukocytes, cancer cells, neural cells, or fibroblasts in response to growth factor stimulation.

In other embodiments, the agent can include a complement antagonist and the cells can be in vasculature of the subject, proximate or about the periphery of a vascular injury. The agent can be administered to the subject to inhibit at least one growth, viability, or mitosis of the cells following growth factor stimulation of the cells. The vascular injury can include at least one of atherogenesis, thrombosis, restinosis, or neointimal formation in the subject.

In still other embodiments, the cells can include tumor or cancer cells and the agent can being selected from the group consisting of a STAT3 inhibitor, an IL-6 inhibitor, a thrombin inhibitor and a combination thereof. The agent can be administered to the cells at an amount effective to inhibit at least one of growth, viability, or mitosis of the cells.

In yet other embodiments, the cells can be endothelial cells and the agent can be selected from the group consisting of a STAT3 inhibitor, an IL-6 inhibitor, a thrombin inhibitor and a combination thereof. The agent can be administered to the endothelial cells at an amount effective to inhibit at least one of growth, viability, or mitosis of the cells.

Another aspect of the application relates to a method of inhibiting neointimal formation in the vasculature of a subject as a result of a vascular injury. The method includes administering to at least one of endothelial cells or smooth muscle cells at the site of or proximate the site of the injured vasculature an agent that inhibits C3aR and/or C5aR signaling of the cells. The agent can be selected from the group consisting of a complement antagonist that substantially reduces the interaction of at least one of C3a or C5a with the C3a receptor (C3aR) and C5a receptor (C5aR).

In some embodiments, the agent can be administered at an amount effect to inhibit at least one of PDGF production by the cells, cell growth, cell viability, or cell mitosis. The agent can also be administered at an amount effective to inhibit at least one of atherogenesis, thrombosis, or restinosis of the subject.

In other embodiments, the agent can be provided on an endovascular device and the endovascular device being administered to the site of vascular injury. The endovascular device can include stents, drug delivery catheters, grafts, and drug delivery balloons utilized in the vasculature of a subject.

BRIEF DESCRIPTION OF THE DRAWINGS

The foregoing and other features of the invention will become more apparent upon a consideration of the following description taken in connection with the accompanying drawings wherein:

FIG. 29 illustrates a chart showing phosphor-Stat3 of serum starved MS-1 cells incubated for 10 min at 37° C. with VEGF-A or IL-6 in the absence or presence of anti-IL-6 mAb or C3aR-A/C5aR-A.

FIG. 30 illustrates plots showing (A) NIH-3T3 cells were in cubated as indicated cell counted over 72 hrs. (B) CTLL IL-2 dependent cells were incubated as indicated and counted over 72 hrs.

FIG. 31 illustrates charts showing: (A) C5a (17 ng/mL) added to NIH-3T3 cells. Bars represent 72 hr counts. (B) PDGF-AA was added to NIH-3T3 cells and a 72 hr culture supernatants were assayed for C5a by ELISA.

FIG. 32 illustrates plots showing SMCs from different knockouts were incubated with PDGF-AA and cell numbers determined each day.

FIG. 33 illustrates charts showing qRT-PCR analysis of C3, factor B and factor D transcripts from HUVEC under hypoxia. A) HUVEC treated with TNF-α, IL-1, and IFN-γ. Blue bars represent samples after treatment. B-C) HUVEC stimulated with C3a (10 ng/ml for 2 hr) or C5a (10 ng/ml for 30 min) Blue bars represent control without C3a/C5a stimulation while red bars represent samples after stimulation. D) HUVEC incubated for 1 hr with FCCP+IAA. Blue bars represent control without hypoxia treatment while yellow bars represent two samples after hypoxia treatment.

FIG. 34 illustrates a chart showing HUVECs stimulated with simvastin, and assayed for DAF and KLF4 mRNA.

DETAILED DESCRIPTION

Figure 1:
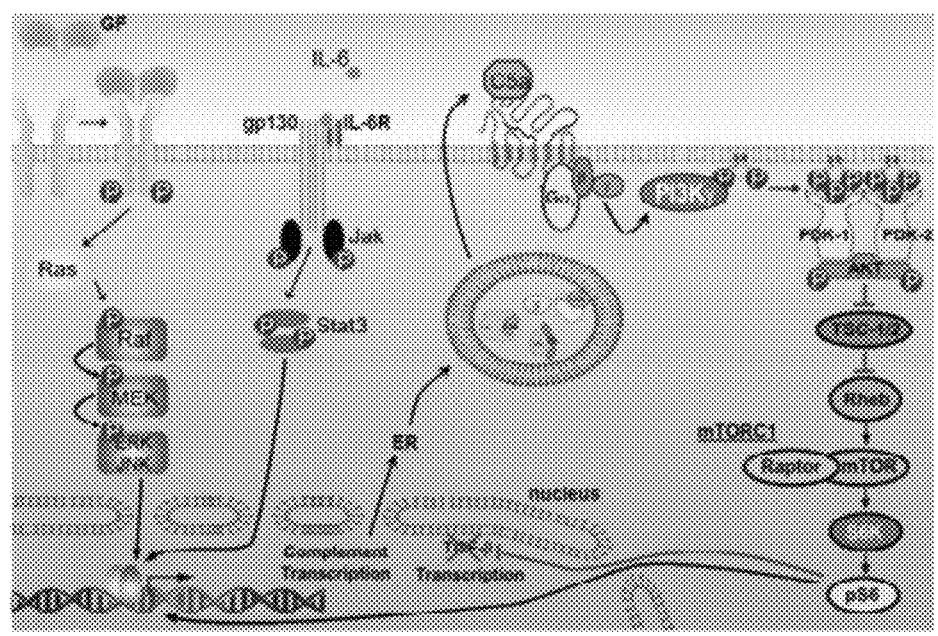
FIG. 1 is a schematic diagram illustrating growth factor and amplification through complement receptor signaling.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the application described herein.

As used herein, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, and all "mimetic" and "peptidomimetic" polypeptide forms.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

As used herein, the term "antibody" refers to whole antibodies, e.g., of any isotype (IgG, IgA, IgM, IgE, etc.), and includes fragments thereof which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies.

As used herein, the term "complementary" refers to the capacity for precise pairing between two nucleobases of a polynucleotide and its corresponding target molecule. For example, if a nucleobase at a particular position of a polynucleotide is capable of hydrogen bonding with a nucleobase at a particular position of a target polynucleotide (the target nucleic acid being a DNA or RNA molecule, for example), then the position of hydrogen bonding between the polynucleotide and the target polynucleotide is considered to be complementary. A polynucleotide and a target polynucleotide are complementary to each other when a sufficient number of complementary positions in each molecule are occupied by nucleobases, which can hydrogen bond with each other. Thus, "specifically hybridizable" and "complementary" are terms which can be used to indicate a sufficient degree of precise pairing or complementarity over a sufficient number of nucleobases such that stable and specific binding occurs between a polynucleotide and a target polynucleotide.

As used herein, the term "subject" refers to any warm-blooded organism including, but not limited to, human beings, rats, mice, dogs, goats, sheep, horses, monkeys, apes, rabbits, cattle, etc.

As used herein, the terms "complement polypeptide" or "complement component" refer to a polypeptide (or a polynucleotide encoding the polypeptide) of the complement system that functions in the host defense against infections and in the inflammatory process. Complement polypeptides constitute target substrates for the complement antagonists provided herein.

As used herein, the term "complement antagonist" refers to a polypeptide, polynucleotide, or small molecule capable of substantially reducing or inhibiting the activity of a complement component.

A complement component can include any one or combination of interacting blood polypeptides or glycoproteins. There are at least 30 soluble plasma polypeptides, in addition to cell surface receptors, which can bind complement reaction products and which can occur on inflammatory cells and cells of the immune system. In addition, there are regulatory membrane proteins that can protect host cells from accidental complement attack. Complement components can include polypeptides that function in the classical pathway, such as C2, polypeptides that function in the alternative pathway, such as Factor B, and polypeptides that function in the lectin pathway, such as MASP-1.

Complement components can also include: any of the "cleavage products" (also referred to as "fragments") that are formed upon activation of the complement cascade; complement polypeptides that are inactive or altered forms of complement polypeptides, such as iC3 and C3a-desArg;

and components indirectly associated with the complement cascade. Examples of such complement components can include, but are not limited to, C1q, C1r, C1s, C2, C3, C3a, C3b, C3c, C3dg, C3g, C3d, C3f, iC3, C3a-desArg, C4, C4a, C4b, iC4, C4a-desArg, C5, C5a, C5a-des-Arg, C6, C7, C8, C9, MASP-1, MASP-2, MBL, Factor B, Factor D, Factor H, Factor I, CR1, CR2, CR3, CR4, properdin, C1Inh, C4 bp, MCP, DAF, CD59 (MIRL), clusterin, HRF, and allelic and species variants of any complement polypeptide.

As used herein, the terms "treatment," "treating," or "treat" refers to any specific method or procedure used for the cure of, inhibition of, prophylaxis of, reduction of, elimination of, or the amelioration of a disease or pathological condition including, for example, age related macular degeneration, cancer, thrombosis, restenosis, neointimal formation, coronary artery disease, atherosclerosis, wounds, central nervous system injuries, peripheral nervous system injuries, and ischemia.

As used herein, the term "effective amount" refers to a dosage of an agent described herein administered alone or in conjunction with any additional therapeutic agents that are effective and/or sufficient to provide treatment of a disease or pathological condition, such as age related macular degeneration, cancer, thrombosis, restenosis, neointimal formation, coronary artery disease, atherosclerosis, wounds, central nervous system injuries, peripheral nervous system injuries, and ischemia. The effective amount can vary depending on the subject, the disease being treated, and the treatment being affected.

As used herein, the term "therapeutically effective amount" refers to that amount of an agent described herein administered alone and/or in combination with additional therapeutic agents that results in amelioration of symptoms associated with a disease or pathological condition, such as age related macular degeneration, cancer, thrombosis, restenosis, neointimal formation, coronary artery disease, atherosclerosis, wounds, central nervous system injuries, peripheral nervous system injuries, and ischemia.

As used herein, the terms "parenteral administration" and "administered parenterally" refers to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the terms "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

As used herein, "Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

Embodiments of this application relate to methods and compositions of modulating growth factor responses of cells, and thereby affecting growth, viability, function, or mitosis of the cells to treat diseases, disorders, and conditions where inhibition or promotion of a growth factor response is desired. The methods can include administering to cells expressing C3a receptor (C3aR) and C5a receptor (C5aR) and at least one growth factor receptor at least one agent that modulates (e.g., inhibits or promotes) C3aR and/or C5aR signaling of the cells.

It was found that C3aR/C5aR signaling resulting from C3a/C5a endogenously produced by the same cell plays a central role in the function of many, if not most, receptor tyrosine kinases (RTKs) and some G protein coupled receptors, (GPCRs), affecting viability and cell proliferation, and tissue homeostasis and function (FIG. 1).

Studies of T cell activation during interaction of antigen presenting dendritic cells (DCs) with cognate T cells showed that both partners locally synthesize complement and that paracrine/autocrine interactions of locally produced C3a/C5a with C3aR/C5aR on both partners provide costimulatory and survival signals to the T cells. We found that the intracellular signaling pathways underlying these processes are essential for phosphoinositide-3 kinase γ (PI-3Kγ) activation and consequent inner leaflet phosphatidylinositol 3,4,5 trisphosphate (PtdIns 3,4,5-$P_3$) generation needed for AKT phosphorylation and downstream signaling to NF-κB. Taken together, the findings indicated that potentiated C3aR/C5aR signaling as contrasted to disabled C3aR/C5aR signaling in T cells (i.e., proliferation vs. PCD) is controlled by surface DAF.

We tested whether this autocrine signaling operates in other cell types and found that this signaling supports the viability of primary cultured ECs, SMCs, embyonic fibroblasts (pMEFs), breast and gastrointestinal epithelial cells (EPCs) as well as more than ten cancer lines of different lineages and that its interruption in all cases induces apoptosis. We found that the mitotic and/or viability effects of seven RTKs and one GPCR depend on autocrine C3aR/C5aR signaling. We also found that IL-6 receptor (IL-6R) and Stat3 are involved in hormone and cytokine growth induction as well as local C5a in the mitotic effects of thrombin.

We also found that RTK signaling interconnects with autocrine C3aR/C5aR signaling and that blockade of either the receptors or their ligands completely abrogated EGF induced growth. Prompted by this result, we performed parallel studies of VEGF-A and PDGF-AA growth induction initially in murine EC lines (bEND.3 and MS-1) and in NIH-3T3 cells, respectively. These experiments surprising yielded near identical results.

Figure 2:
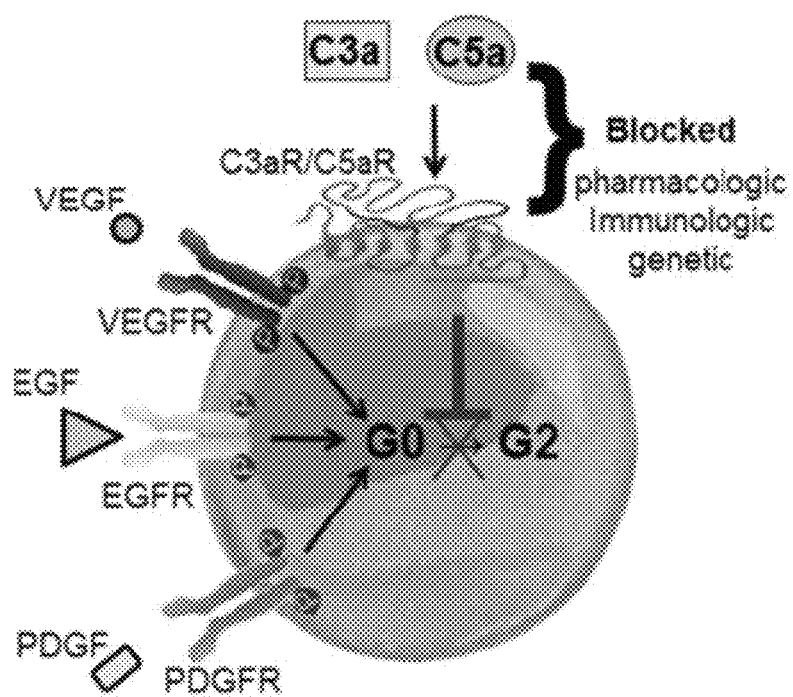
FIG. 2 is a schematic diagram illustrating that when C3aR/C5aR signal transduction is antagonized either pharmacologically, immunologically, or genetically, cell growth and progression from G0 to G2 is blocked.
Figure 3:
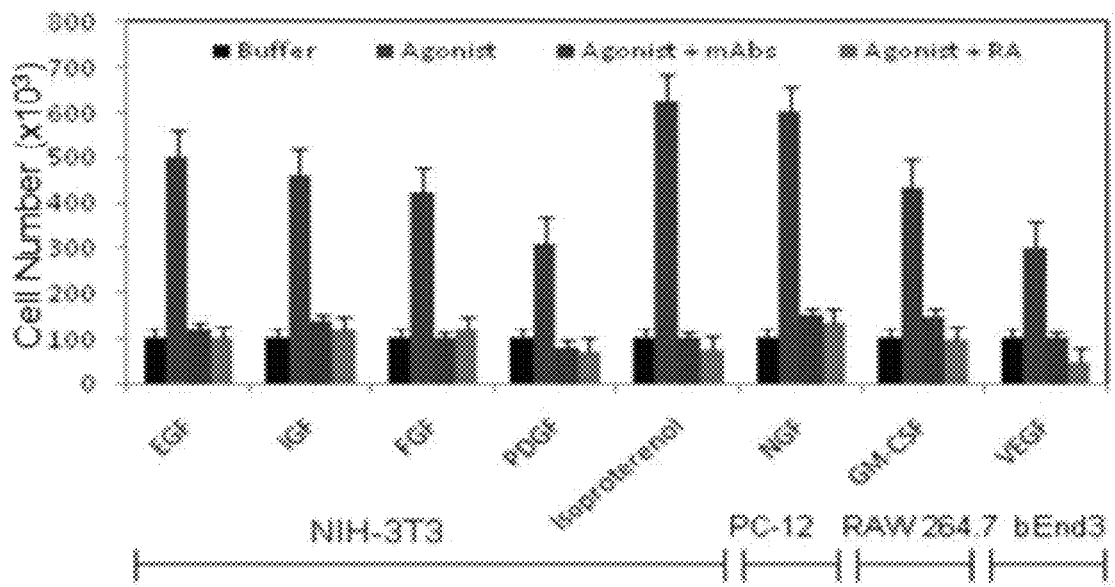
FIG. 3 illustrates a chart showing the effect of C3aR/C5aR antagonism on 7 RTKs and β1-adreneric receptor in respective cell types.

Because this dependence of growth factor responsiveness on C3aR/C5aR signaling could be indirect, i.e., a consequence of its requirement for viability, we performed cell cycle assays. Adding C5a to serum starved NIH-3T3 cells, bEND.3 ECs, or TC-1 cancer cells caused transition from G0 into G2 identically to that of adding EGF to NIH-3T3 or TC-1 cells or adding VEGF-A to bEND.3 ECs (FIGS. 2 and 3). Importantly, including C3aR-A/C5aR-A together with EGF or with VEGF-A markedly blunted or abolished triggering of the cell cycle by EGF and VEGF-A, suggesting that autocrine C3aR/C5aR signals not only limit apoptosis but are needed for cell cycle progression.

To gain mechanistic insight, we focused on VEGF-A growth induction through VEGFR2 in ECs. As a first test of whether VEGFR2 growth induction is interconnected with upregulated C3aR/C5aR signaling, we examined the effect of added VEGF-A on local complement production by the MS-1 and bEND.3 EC cell lines. ELISAs of their culture supernatants showed that VEGF-A increased local C3a as well as C5a production, both ~8-fold and that both increases were abolished by the inclusion of C3aR-A/C5aR-A. Adding C5a to serum starved HUVEC caused transition from G0 into G2 identically to adding VEGF-A, whereas C3aR/C5aR blockade prevented VEGF-A triggering of the cell cycle. These findings together with the dependence VEGF-A growth induction on C3aR/C5aR signaling indicated that VEGFR2 signals amplify C3aR/C5aR signal transduction and that amplification of this autocrine GPCR signaling integrates with VEGFR2 growth signals. Consistent with the increased local C3a/C5a production, VEGF-A upregulated mRNA transcripts of all of the components/receptors associated with autocrine C3aR/C5aR signaling in primary cultured aortic ECs, whereas antagonizing C3aR/C5aR abrogated the up-regulations and induced markers of apoptosis.

To determine if the linkage between VEGF-A and C3aR/C5aR signaling in ECs involves IL-6, we incubated MS-1 ECs with 1) VEGF-A alone, IL-6 alone, or VEGF-A plus anti-IL-6 mAb, or with 2) IL-6 alone or IL-6 plus C3aR-A/C5aR-A, and assayed cell growth. IL-6 induced EC growth comparably to VEGF-A and VEGF-A's growth induction was abolished by anti-IL-6 mAb. The EC induced growth by IL-6, like that of VEGF-A, was abolished by C3aR-A/C5aR-A. Both VEGF-A and IL-6 induced Stat3 phosphorylation. Importantly, the Stat3 phosphorylation in both cases was abolished by C3aR/C5aR antagonism. Relevant to this, VEGF-A treatment or WT aortic ECs upregulated C3/C5 and increased local C3a/C5a generation as found for MS-1 ECs, but neither change occurred in the presence of anti-IL-6 mAb or the JAK1 inhibitor. These findings thus indicate that VEGFR2 signaling interconnects with C3aR/C5aR signaling via a process involving induction of IL-6 and activation of Stat3.

We surprisingly have found that the thrombin specific inhibitors ANGIOMAX, and antithrombin, as well as other thrombin specific inhibitors PPACK and FM19 virtually abolish T cell activation in response anti-CD3/28 stimulation as well as abolish the proliferation of ECs in response to VEGF-A stimulation. We additionally have found that both T cell activation and VEGF induced EC growth induction are blocked by the MMP-9 and −1 inhibitor. Since some MMPs (MMP-9) is/are constitutively expressed and prothrombin synthesis and secretion might be induced by VEGF-A, prothrombin can cleaved to thrombin by an MMP, e.g., MMP-9 and thrombin, in turn, generates C5a from locally produced C5. The MMP inhibitor alternatively could exert its inhibitory effect on VEGF-A induced EC growth by the pathway that couples C3aR/C5aR signal transduction back to VEGFR2.

Accordingly, based at least in part on these findings, in some embodiments of the application a population of cells expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts, can be contacted (e.g., directly or locally) with a therapeutically effective amount of an agent that modulates (e.g., inhibits or promotes) C3aR and/or C5aR signaling of the cells and modulates (e.g., inhibits or promotes) response of the cells to a growth factor. This modulation of growth factor response can affect viability, function, or mitosis of the cells and treat diseases, disorders, and conditions where inhibition or promotion of a growth factor response is desired.

In some embodiments, a growth factor response (e.g., function, growth, viability, and/or mitosis) of a cell expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts, can be inhibited by administering to the cell an agent that inhibits C3aR and/or C5aR signaling of the cells. The agent can be selected from the group consisting of a complement antagonist that inhibits or substantially reduces the interaction of at least one of C3a or C5a with the C3a receptor (C3aR) and C5a receptor (C5aR), an IL-6/STATS signaling pathway antagonist, a thrombin inhibitor and combinations thereof.

By inhibiting or substantially reducing the activity of a complement component, it is meant that the activity of the complement component may be entirely or partly diminished. For example, an inhibition or reduction in the functioning of a C3/C5 convertase may prevent cleavage of C5 and C3 into C5a and C3a, respectively. An inhibition or reduction in the functioning of C5, C3, C5a and/or C3a polypeptides may reduce or eliminate the ability of C5a and C3a to bind C5aR and C3aR, respectively. An inhibition or reduction in Factor B, Factor D, properidin, Bb, Ba and/or any other protein of the complement pathway that is used in the formation of C3 convertase, C5 convertase, C5, C3, C5a and/or C3a may reduce or eliminate the ability of C5a and C3a to be formed and bind to C5aR and C3aR, respectively. Additionally, an inhibition or reduction in the functioning of a C5aR or C3aR may similarly reduce or eliminate the ability of C5a and C3a to bind C5aR and C3aR, respectively.

In an aspect of the application, the at least one complement antagonist can include an antibody or antibody fragment directed against a complement component that can affect or inhibit the formation of C3a and/or C5a (e.g., anti-Factor B, anti-Factor D, anti-C5, anti-C3, ant-C5 convertase, and anti-C3 convertase) and/or reduce C5a/C3a-C5aR/C3aR interactions (e.g., anti-C5a, anti-C3a, anti-C5aR, and C3aR antibodies). In one example, the antibody or antibody fragment can be directed against or specifically bind to an epitope, an antigenic epitope, or an immunogenic epitope of a C5, C3, C3a, C5a, C5aR, C3aR, C5 convertase, and/or C3 convertase. The term "epitope" as used herein can refer to portions of C5, C3, C3a, C5a, C5aR, C3aR, C5 convertase, and/or C3 convertase having antigenic or immunogenic activity. An "immunogenic epitope" as used herein can include a portion of a C5, C3, C3a, C5a, C5aR, C3aR, C5 convertase, and/or C3 convertase that elicits an immune response in a subject, as determined by any method known in the art. The term "antigenic epitope" as used herein can include a portion of a polypeptide to which an antibody can immunospecifically bind as determined by any method well known in the art.

Examples of antibodies directed against C5, C3, C3a, C5a, C5aR, C3aR, C5 convertase, and/or C3 convertase are known in the art. For example, mouse monoclonal antibodies directed against C3aR can include those available from Santa Cruz Biotechnology, Inc. (Santa Cruz, Calif.). Monoclonal anti-human C5aR antibodies can include those available from Research Diagnostics, Inc. (Flanders, N.J.). Monoclonal anti-human/anti-mouse C3a antibodies can include those available from Fitzgerald Industries International, Inc. (Concord, Me.). Monoclonal anti-human/anti-mouse C5a antibodies can include those available from R&D Systems, Inc. (Minneapolis, Minn.).

In some embodiments, the complement antagonist can include purified polypeptide that is a dominant negative or competitive inhibitor of C5, C3, C3a, C5a, C5aR, C3aR, C5 convertase, and/or C3 convertase. As used herein, "dominant negative" or "competitive inhibitor" refers to variant forms of a protein that inhibit the activity of the endogenous, wild type form of the protein (i.e., C5, C3, C3a, C5a, C5aR, C3aR, C5 convertase, and/or C3 convertase). As a result, the dominant negative or competitive inhibitor of a protein promotes the "off" state of protein activity. In the context of the present invention, a dominant negative or competitive inhibitor of C5, C3, C3a, C5a, C5aR, C3aR, C5 convertase, and/or C3 convertase is a C5, C3, C3a, C5a, C5aR, C3aR, C5 convertase, and/or C3 convertase polypeptide, which has been modified (e.g., by mutation of one or more amino acid residues, by posttranscriptional modification, by posttranslational modification) such that the C5, C3, C3a, C5a, C5aR, C3aR, C5 convertase, and/or C3 convertase inhibits the activity of the endogenous C5, C3, C3a, C5a, C5aR, C3aR, C5 convertase, and/or C3 convertase.

In some embodiments, the competitive inhibitor of C5, C3, C3a, C5a, C5aR, C3aR, C5 convertase, and/or C3 convertase can be a purified polypeptide that has an amino acid sequence, which is substantially similar (i.e., at least about 75%, about 80%, about 85%, about 90%, about 95% similar) to the wild type C5, C3, C3a, C5a, C5aR, C3aR, C5 convertase, and/or C3 convertase but with a loss of function. The purified polypeptide, which is a competitive inhibitor of C5, C3, C3a, C5a, C5aR, C3aR, C5 convertase, and/or C3 convertase, can be administered to a cell expressing C5aR and/or C3aR.

It will be appreciated that antibodies directed to other complement components used in the formation of C5, C3, C5a, C3a, C5 convertase, and/or C3 convertase can be used in accordance with the method described herein to reduce and/or inhibit interactions C5a and/or C3a with C5aR and C3aR. The antibodies can include, for example, known Factor B, properdin, and Factor D antibodies that reduce, block, or inhibit the formation of C5a and/or C3a.

In some embodiments, the complement antagonist can include RNA interference (RNAi) polynucleotides to induce knockdown of an mRNA encoding a complement component. For example, an RNAi polynucleotide can comprise a siRNA capable of inducing knockdown of an mRNA encoding a C3, C5, C5aR, or C3aR polypeptide.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (I) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Examples of a siRNA molecule directed to an mRNA encoding a C3a, C5a, C5aR, or C3aR polypeptide are known in the art. For instance, human C3a, C3aR, and C5a siRNA is available from Santa Cruz Biotechnology, Inc. (Santa Cruz, Calif.). Additionally, C5aR siRNA is available from Qiagen, Inc. (Valencia, Calif.). siRNAs directed to other complement components, including C3 and C5, are known in the art.

In other embodiments, the RNAi construct can be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Such hairpin RNAs are engineered in cells or in an animal to ensure continuous and stable suppression of a desired gene. It is known in the art that siRNAs can be produced by processing a hairpin RNA in the cell.

In yet other embodiments, a plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the a recombinant vector can have the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Examples RNAi constructs that specifically recognize a particular gene or a particular family of genes, can be selected using methodology outlined in detail above with respect to the selection of antisense oligonucleotide. Similarly, methods of delivery RNAi constructs include the methods for delivery antisense oligonucleotides outlined in detail above.

In some embodiments, a lentiviral vector can be used for the long-term expression of a siRNA, such as a short-hairpin RNA (shRNA), to knockdown expression of C5, C3, C5aR, and/or C3aR in cells expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts. Although there have been some safety concerns about the use of lentiviral vectors for gene therapy, self-inactivating lentiviral vectors are considered good candidates for gene therapy as they readily transfect mammalian cells.

It will be appreciated that RNAi constructs directed to other complement components used in the formation of C5, C3, C5a, C3a, C5 convertase, and/or C3 convertase components can be used in accordance with the method described herein to reduce and/or inhibit interactions C5a and/or C3a with C5aR and C3aR on the cells expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts. The RNAi constructs can include, for example, known Factor B, properdin, and Factor D siRNA that reduce expression of Factor B, properdin, and Factor D.

Moreover, it will be appreciated that other antibodies, small molecules, and/or peptides that reduce or inhibit the formation of C5, C3, C5a, C3a, C5 convertase, and/or C3 convertase and/or that reduce or inhibit interactions C5a and/or C3a with C5aR and C3aR on the cells expressing C3a receptor (C3aR) and C5a receptor (C5aR) and at least one growth factor receptor (e.g., RTK) can be used as a complement antagonist in accordance with the method described herein. These other complement antagonists can be administered to the cells expressing C3a receptor (C3aR) and C5a receptor (C5aR) and at least one growth factor receptor (e.g., RTK) at amount effective to inhibit a growth factor response. Example of such other complement antagonists include C5aR antagonists, such as AcPhe[Orn-Pro-D-cyclohexylalanine-Trp-Arg, prednisolone, and infliximab (Woodruff et al., The Journal of Immunology, 2003, 171: 5514-5520), hexapeptide MeFKPdChaWr (March et al., Mol Pharmacol 65:868-879, 2004), PMX53 and PMX205, and N-[(4-dimethylaminophenyl)methyl]-N-(4-isopropylphenyl)-7-methoxy-1,2,3,4-tetrahydronaphthalen-1-carboxamide hydrochloride (W-54011) (Sumichika et al., J. Biol. Chem., Vol. 277, Issue 51, 49403-49407, Dec. 20, 2002), and a C3aR antagonist, such as SB 290157 (Ratajczak et al., Blood, 15 Mar. 2004, Vol. 103, No. 6, pp. 2071-2078).

In other embodiments, the agent that inhibits C3aR and/or C5aR signaling in a cell expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts, can include an IL-6/STAT3 signaling pathway antagonist that substantially decreases or inhibits the expression and/or functional activity of a component of the IL-6/STAT3 signaling pathway in the cell. The functional activity of the IL-6/STAT3 signaling pathway can be suppressed, inhibited, and/or blocked in several ways including: direct inhibition of the activity of IL-6 and/or STAT3 (e.g., by using neutralizing antibodies, small molecules or peptidomimetics, dominant negative polypeptides); inhibition of genes that express IL-6 and/or STAT-3 (e.g., by blocking the expression or activity of the genes and/or proteins); activation of genes and/or proteins that inhibit one or more of the functional activity of IL-6 and/or STAT3 (e.g., by increasing the expression or activity of the genes and/or proteins); inhibition of genes and/or proteins that are downstream mediators of the iNOS expression (e.g., by blocking the expression and/or activity of the mediator genes and/or proteins); introduction of genes and/or proteins that negatively regulate one or more of functional activity of IL-6 and/or STAT3 (e.g., by using recombinant gene expression vectors, recombinant viral vectors or recombinant polypeptides); or gene replacement with, for instance, a hypomorphic mutant of STAT-3 (e.g., by homologous recombination, overexpression using recombinant gene expression or viral vectors, or mutagenesis).

In an embodiment of the application, the IL-6/STAT3 signaling pathway antagonist is an IL-6 antagonist. In some aspects, the IL-6 antagonist can include a humanized IL-6 receptor-inhibiting monoclonal antibody. In certain aspects, the IL-6 antagonist is the product tocilizumab (a descriptive name sold under the trademark ACTEMRA by Roche, Switzerland). In other aspects, the IL-6 antagonist can include a vaccine that when administered to a subject generates IL-6 antibodies in the subject. An example of such a vaccine is disclosed in Fosergau et al. Journal of Endocrinology (2010) 204, 265-273.

In another embodiment, the IL-6/STAT3 signaling pathway antagonist is a tyrosine kinase inhibitor. Exemplary tyrosine kinase inhibitors for use in the present invention include but are not limited to tyrphostins, in particular AG-490, and inhibitors of Jak, Src, and BCR-Abl tyrosine kinases. Other tyrphostins suitable for use herein include, but are not limited to AG17, AG213 (RGS0864), AG18, AG82, AG494, AG825, AG879, AG1112, AG1296, AG1478, AG126, RG13022, RG14620, AG555, and related compounds. In certain aspects, a BCR-Abl tyrosine kinase inhibitor for use herein can include the product imatinib mesilate (a descriptive name sold under the trademark GLEEVEC® by Novartis, Switzerland).

In a further embodiment, the IL-6/STAT3 signaling pathway antagonist is an HMG CoA reductase inhibitor (3-hydroxymethylglutaryl coenzyme A reductase inhibitors) (e.g., statin). HMG-CoA (3-hydroxy methylglutaryl coenzyme A) reductase is the microsomal enzyme that catalyzes the rate limiting reaction in cholesterol biosynthesis (HMG-CoA Mevalonate.

Statins that can be used for administration, or co-administration with other agents described herein include, but are not limited to, simvastatin (U.S. Pat. No. 4,444,784), mevistatin, lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, U.S. Pat. Nos. 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860 U.S. Pat. Nos. 4,940,800, 4,940,727, 4,939,143, 4,929,620, 4,923,861, 4,906,657, 4,906,624 and 4,897,402, the disclosures of which patents are incorporated herein by reference.

In yet another embodiment, the IL-6/STAT3 signaling pathway antagonist can be a STAT3 inhibitor. Examples of STAT3 inhibitors are described in U.S. Patent Application No. 2010/0041685 and can include 4-[3-(2,3-dihydro-1,4-benzodioxin-6-yl)-3-oxo-1-propen-1-yl]benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl]benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidi-nylidene)methyl]-2-furyl}benzoic acid; a functionally active derivative thereof and a mixture thereof. Other examples of STAT3 inhibitors are described in WO 2010/118309 and in G. Zinzalla et al. Bioorg. Med. Chem. Lett. 20 (2010)7029-7032.

In other embodiments, the agent that inhibits C3aR and/or C5aR signaling in a expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts, can include thrombin inhibitor that substantially decreases or inhibits thrombin cleavage of C3 and/or C5 generated by the cell to C3a and C5a that can bind to C3aR and C5aR.

Thrombin inhibitors that can used in the methods described herein include those which inhibit thrombosis, including but not limited to those described in U.S. Pat. Nos. 5,536,708, 5,510,369, 5,672,582, 5,714,485, 5,629,324 (e.g. N'-[[1-(Aminoiminomethyl)-4-piperidinyl]methyl]-N-(3,3-diphenylpropionyl)-L-proline amide), U.S. Pat. No. 5,668, 289 (e.g. 3-(2-Phenethylamino)-6-methyl-1-(2-amino-6-methyl-5-methylenecarboxamidomethylpyridinyl)-2-pyridinone), U.S. Pat. Nos. 5,744,486, 5,798,377, WO 9631504, WO9611941, WO9606832, WO9606849, WO9420467, WO 9632110, U.S. Pat. No. 4,496,653, WO 9715190, and WO 9740024, e.g. 3-(2-Phenylethylamino)-6-methyl-1-(2-amino-6-methyl-5-methylenecarboxam-idomethylpyridinyl)-2-pyrazinone, the contents of which are hereby incorporated by reference.

Other examples of thrombin inhibitors include low molecular weight peptide-based thrombin inhibitors. The term "low molecular weight peptide-based thrombin inhibitors" will be well understood by one skilled in the art to include thrombin inhibitors with one to four peptide linkages, and/or with a molecular weight below 1000, and includes those described in the review paper by Claesson in Blood Coagul. Fibrin. (1994) 5:411, as well as those disclosed in U.S. Pat. No. 4,346,078; International Patent Applications WO 93/11152, WO 95/23609, WO 95/35309, WO 96/25426, WO 94/29336, WO 93/18060 and WO 95/01168; and European Patent Nos. 648 780, 468 231, 559 046, 641779, 185 390, 526 877, 542 525, 195 212, 362 002, 364 344, 530 167, 293 881, 686 642, 669 317 and 601 459.

In some embodiments, the thrombin inhibitor can be selected from the group consisting of ANGIOMAX, PPACK, and FM19.

The at least one agent that inhibits C3aR and/or C5aR signaling can be administered to the cells in vivo or in vitro to inhibit a growth factor response of the cells. The cell can be derived from a human subject, from a known cell line, or from some other source. Examples of cells expressing C3a receptor (C3aR) and C5a receptor (C5aR) and at least one growth factor receptor (e.g., RTK) include smooth muscle cells, endothelial cells, leukocytes, cancer cells, neural cells, or fibroblasts that are located in, for example, in tissue of a human subject. The cell may be isolated or, alternatively, associated with any number of identical, similar, or different cell types.

In some embodiments, the agent that inhibits at least one of C3aR and/or C5aR signaling in the cell expressing C3aR and C5aR may be used to treat animals and patients with aberrant angiogenesis resulting from or mediated by growth factors, such as VEGF. Such aberrant angiogenesis, outside the field of cancer treatment, can include or be associated with arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the compositions described herein, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Another example of a disease mediated by angiogenesis is ocular neovascular disease. This disease is characterized by invasion of new blood vessels into the structures of the eye, such as the choroid, retina, or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stipulatory activity. VEGF expression in human coronary atherosclerotic lesions has been demonstrated. This evidences the pathophysiological significance of VEGF in the progression of human coronary atherosclerosis, as well as in recanalization processes in obstructive coronary diseases. The compositions and methods of this application therefore provide an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate.

Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the present invention. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the agents described herein, as disclosed in, e.g., U.S. Pat. No. 5,712,291 (specifically incorporated herein by reference), that unified benefits result from the application of anti-angiogenic strategies to the treatment of angiogenic diseases.

The agent that inhibits at least one of C3aR and/or C5aR signaling in the cell expressing C3aR and C5aR can also be utilized in the treatment of tumors. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs.

The agent that inhibits at least one of C3aR and/or C5aR signaling in the cell expressing C3aR and C5aR is broadly applicable to the treatment of any tumor or cancer having a vascular component as well as any tumor or cancer cell that expresses C3aR and/or C5aR. In using the agent that inhibits at least one of C3aR and/or C5aR signaling in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using an agent that inhibits at least one of C3aR and/or C5aR signaling.

Agents that inhibit at least one of C3aR and/or C5aR signaling in the cells expressing C3aR and C5aR can be use in the treatment of any patient that presents with a solid tumor. In light of the specific properties of the agents described herein, the agents will have reduced side effects. Particular advantages will result in the maintenance or enhancement of host immune responses against the tumor, as mediated by macrophages, and in the lack of adverse effects on bone tissue. The agents can be the anti-angiogenic therapy of choice for the treatment of pediatric cancers and patients having, or at risk for developing, osteoporosis and other bone deficiencies.

The agents that inhibit at least one of C3aR and/or C5aR signaling are also intended for use in preventative or prophylactic treatments. These aspects include the ability to treat patients presenting with a primary tumor who may have metastatic tumors, or tumor cells in the earlier stages of metastatic tumor seeding. As an anti-angiogenic strategy, the agents may also be used to prevent tumor development in subjects at moderate or high risk for developing a tumor, as based upon prognostic tests and/or close relatives suffering from a hereditary cancer.

The foregoing anti-angiogenic treatment methods and uses will generally involve the administration of the pharmaceutically effective composition comprising to the animal or patient by any route of administration that allows the agent to localize to the angiogenic site or sites. Such administration routes can include direct administration, including tumor or intratumoral vascular endothelial cells, will be acceptable. Therefore, other suitable routes of delivery include oral, rectal, nasal, topical, and vaginal. U.S. Pat. No. 5,712,291, is specifically incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the agents that inhibit at least one of C3aR and/or C5aR signaling in an amount(s) and for a period of time(s) effective to exert anti-angiogenic and/or anti-tumor effects.

Therapeutically effective doses of the agents that inhibit at least one of C3aR and/or C5aR signaling are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors are widely used in pre-clinical testing.

In using the agents that inhibit at least one of C3aR and/or C5aR signaling in anti-angiogenic therapies, one can also draw on other published data in order to assist in the formulation of doses for clinical treatment. For instance, although the agents and methods of the present invention have distinct advantages over those in the art, the information in the literature concerning treatment with other polypeptides and tyrosine kinase inhibitors can still be used in combination with the data and teaching in the present application to design and/or optimize treatment protocols and doses.

Any dose, or combined medicament of the agents that inhibit at least one of C3aR and/or C5aR signaling, that results in any consistently detectable anti-angiogenic effect, inhibition of metastasis, tumor vasculature destruction, tumor thrombosis, necrosis and/or general anti-tumor effect will define a useful invention. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-angiogenic and/or tumor effects of the dose, or combined therapy of the agents that inhibit at least one of C3aR and/or C5aR signaling, are towards the low end of the intended therapeutic range, it may be that this therapy is still equally or even more effective than all other known therapies in the context of the particular tumor target or patient. It is unfortunately evident to a clinician that certain tumors and conditions cannot be effectively treated in the intermediate or long term, but that does not negate the usefulness of the present therapy, particularly where it is at least about as effective as the other strategies generally proposed.

In designing appropriate doses of the agents that inhibit at least one of C3aR and/or C5aR signaling for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m2) between the experimental animal and the human patient. All such calculations are well known and routine to those of ordinary skill in the art.

It will be understood that lower doses may be more appropriate in combination with other agents, and that high doses can still be tolerated.

Formulation of pharmaceutical compounds for use in the modes of administration noted above (and others) are described, for example, in *Remington's Pharmaceutical Sciences* ($18^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the agents that inhibit at least one of C3aR and/or C5aR signaling can be provided in ophthalmic preparation that can be administered to the subject's cornea or eye. The ophthalmic preparation can contain the agents that inhibit at least one of C3aR and/or C5aR signaling in a pharmaceutically acceptable solution, suspension or ointment. Some variations in concentration will necessarily occur, depending on the particular complement antagonist employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

The agents that inhibit at least one of C3aR and/or C5aR signaling can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin include, for example, ointments, creams, gels and pastes comprising the complement antagonist in a pharmaceutical acceptable carrier. The formulation of complement antagonists for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

In some embodiments, the agent being selected from the group consisting of a STATS IL-6 signaling pathway antagonist, a thrombin inhibitor and a combination thereof. The agent can be administered to the cells of the tumor or aberrant angiogenic tissue at amount effective to inhibit at least one of growth, viability, or mitosis of the cells.

In other embodiments, the agent that inhibits at least one of C3aR and/or C5aR signaling in the cell expressing C3aR and C5aR may be used to treat animals and patients with vascular diseases that cause obstruction of the vascular system as result of growth factor responses, such as PDGF. Such diseases can, for example, result from neointimal accumulation on a vascular surface as a result of a vascular injury and PDGF generation. Representative examples of such diseases include artherosclerosis or atherogenesis of all vessels (around any artery, vein or graft) including, but not restricted to: the coronary arteries, aorta, iliac arteries, carotid arteries, common femoral arteries, superficial femoral arteries, popliteal arteries, and at the site of graft anastomosis; vasospasms (for example, coronary vasospasms and Raynaud's Disease); restenosis (obstruction of a vessel at the site of a previous intervention such as balloon angioplasty, bypass surgery, stent insertion and graft insertion); thrombosis inflammatory and autoimmune conditions (for example, Temporal Arteritis, vasculitis).

Briefly, in vascular diseases such as atherosclerosis, white cells, specifically monocytes and T lymphocytes adhere to endothelial cells, especially at locations of arterial branching in response to PDGF signalling. After adhering to the endothelium, leukocytes migrate across the endothelial cell lining in response to chemostatic stimuli, and accumulate in the intima of the arterial wall, along with smooth muscle cells. This initial lesion of athersosclerosis development is known as the "fatty streak". Monocytes within the fatty streak differentiate into macrophages; and the macrophages and smooth muscle cells progressively take up lipids and lipoprotein to become foam cells.

As macrophages accumulate, the overlying endothelium becomes mechanically disrupted and chemically altered by oxidized lipid, oxygen-derived free radicals and proteases which are released by macrophages. Foam cells erode through the endothelial surface causing micro-ulcerations of the vascular wall. Exposure of potentially thrombogenic subendothelial tissues (such as collagen and other proteins) to components of the bloodstream results in adherence of platelets to regions of disrupted endothelium. Platelet adherence and other events triggers the elaboration and release of growth factors into this milieu, including platelet-derived growth factor (PDGF), platelet activating factor (PAF), and interleukins 1 and 6 (IL-1, IL-6). These paracrine factors are thought to stimulate vascular smooth muscle cell (VSMC) migration and proliferation.

In addition to PDGF, IL-1 and IL-6, other mitogenic factors are produced by cells which infiltrate the vessel wall including: transforming growth factor β (TGF-β), fibroblast growth factor (FGF), thrombospondin, serotonin, thromboxane $A_2$, norepinephrine, and angiotensin II. This results in the recruitment of more cells, elaboration of further extracellular matrix and the accumulation of additional lipid. This progressively enlarges the atherosclerotic lesion until it significantly encroaches upon the vascular lumen. Initially, obstructed blood flow through the vascular tube causes ischemia of the tissues distal to the atherosclerotic plaque only when increased flow is required—later as the lesion further blocks the artery, ischemia occurs at rest.

Macrophages in the enlarging atherosclerotic plaque release oxidized lipid, free radicals, elastases, and collagenases that cause cell injury and necrosis of neighbouring tissues. The lesion develops a necrotic core and is transformed into a complex plaque. Complex plaques are unstable lesions that can: break off causing embolization; local hemorrhage (secondary to rupture of the vasa vasora supplying the plaque which results in lumen obstruction due to rapid expansion of the lesion); or ulceration and fissure formation (this exposes the thrombogenic necrotic core to the blood stream producing local thrombosis or distal embolization). Even should none of the above sequel occur, the adherent thrombus may become organized and incorporated into the plaque, thereby accelerating its growth. Furthermore, as the local concentrations of fibrinogen and thrombin increase, proliferation of vascular smooth muscle cells within the media and intima is stimulated; a process which also ultimately leads to additional narrowing of the vessel.

Agents that inhibit C3aR and/or C5aR signaling can be administered to cells expressing C3aR and/or C5aR, such as vascular endothelial cells, smooth muscle cells, and macrophages, to inhibit PDGF mediated accumulation of plaque. In some embodiments, the agent can administered directly to the cells using, for example, a medical device that can be delivered to the vasculature.

The medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

In some embodiments, the agent can include a complement antagonist that is coated or provided on an endovascular device and is used to treat a vascular injury. The vascular injury can include, for example, atherosclerosis, thrombosis, stenosis, restenosis, and/or neoinitimal accumulation that results from vascular injury. The complement antagonist can include DAF or an antibody directed against at least one of C3, C5, C3 convertase, C5 convertase, C3a, C5a, C3aR, or C5aR. The complement antagonist can be administered at amount effective to inhibit neointimal accumulation and/or stenosis of the vasculature.

In other embodiments of the application, a growth factor response (e.g., function, growth, viability, and/or mitosis) of a cell expressing C3a receptor (C3aR) and C5a receptor (C5aR) and at least one growth factor receptor (e.g., RTK), such as smooth muscle cells, endothelial cells, leukocytes, cancer cells, neural cells, or fibroblasts, can be promoted or stimulated by administering to the cell an agent that promotes or stimulates C3aR and/or C5aR signaling of the cells. The agent can be selected from the group consisting of C3, C5, C3a, C5a, a C3aR agonist, a C5aR agonist, a DAF antagonist, or combination thereof.

Promotion or stimulation of C3aR and/or C5aR activation in cells expressing C3a receptor (C3aR) and C5a receptor (C5aR) and at least one growth factor receptor (e.g., RTK), such as smooth muscle cells, endothelial cells, neural cells, or fibroblasts induce a growth factor response in the cells can be used to stimulate, promote, and/or enhance growth, viability, function, or mitosis of the cells in response to growth factor stimulation.

In some embodiments, an agent that promotes or stimulates C3aR and/or C5aR signaling can be used to treat ischemic disorders and/or tissue injury in a mammalian subject. The ischemic disorder and/or tissue injury can comprise, for example, a peripheral vascular disorder, a pulmonary embolus, a venous thrombosis, a myocardial infarction, a transient ischemic attack, unstable angina, cerebral vascular ischemia, a reversible ischemic neurological deficit, ischemic kidney disease, or a stroke disorder.

The ischemic disorder can also comprise an iatrogenically induced ischemic disorder. The iatrogenic ischemic disorder can result from a subject undergoing, for example, angioplasty, heart surgery, lung surgery, spinal surgery, brain surgery, vascular surgery, abdominal surgery, kidney surgery, or organ transplantation surgery. The organ transplantation can comprise heart, lung, pancreas, kidney, or liver translation surgery.

The agent that promotes or stimulates C3aR and/or C5aR signaling of the cells can be administered directly to or about the periphery of ischemic tissue in order to promote or stimulate angiogenesis of the ischemic tissue. In one aspect of the invention, the agent that promotes or stimulates C3aR and/or C5aR signaling of the cells can be delivered to or about the periphery of the ischemic tissue by administering the agent neat or in a pharmaceutical composition to or about the ischemic tissue. The pharmaceutical composition can provide localized release of the agent to the ischemic tissue or cells being treated. Pharmaceutical compositions in accordance with the invention will generally include an amount of the agent that promotes or stimulates C3aR and/or C5aR signaling of the cells or variants thereof admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards.

The pharmaceutical composition can be in a unit dosage injectable form (e.g., solution, suspension, and/or emulsion). Examples of pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

Pharmaceutical "slow release" capsules or "sustained release" compositions or preparations may be used and are generally applicable. Slow release formulations are generally designed to give a constant drug level over an extended period and may be used to deliver the agent. The slow release formulations are typically implanted in the vicinity of the ischemic tissue site, for example, at the site of a cell expressing C3aR and/or C5aR in or about the ischemic tissue.

Examples of sustained-release preparations include semipermeable matrices of solid hydrophobic polymers containing the agent that promotes or stimulates C3aR and/or C5aR signaling of the cells, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated agent remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the agent that promotes or stimulates C3aR and/or C5aR signaling of the cells. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

In another aspect, the agent that promotes or stimulates C3aR and/or C5aR signaling of the cells can be administered directly to or about the periphery of the ischemic tissue by introducing an agent into target cells that causes, increases, and/or upregulates expression of at least one of C3, C5, C3a, C5a, a C3aR agonist, or C5aR agonist in or about the periphery of the ischemic tissue. The at least one of at least one of C3, C5, C3a, C5a, a C3aR agonist, or C5aR agonist is expressed in or about the periphery of the ischemic tissue can be an expression product of a genetically modified cell. The target cells can include cells within or about the periphery of the ischemic tissue or ex vivo cells that are biocompatible with the ischemic tissue being treated. The biocompatible cells can also include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the ischemic tissue being treated.

In other embodiments, the agent that promotes or stimulates C3aR and/or C5aR signaling of the cells can be administered in combination with a growth factor that promotes angiongenesis or vasculogenesis of the ischemic tissue, mitigates apoptosis of cells of the ischemic tissue, and/or promotes repair of the ischemic tissue. The growth factor can include, for example, VEGF, NGF, GM-SCF, EGF, FGF, IGF, BDNF, BMP, SDF-1, and/or HGF.

In other embodiments, an agent that promotes or stimulates C3aR and/or C5aR signaling can be used to treat wounds in a mammalian subject. The wounds treated by the method and/or compositions can include any injury to any portion of the body of a subject (e.g., internal wound or external wound) including: acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries, such as cuts, incisions, excoriations, injuries sustained as result of accidents, ulcers, such as pressure ulcers, diabetic ulcers, plaster ulcers, and decubitus ulcer, post-surgical injuries. The wound can also include chronic conditions or wounds, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; tumor associated wounds.

It will be appreciated that the application is not limited to the preceding wounds or injuries and that other wounds or tissue injuries whether acute and/or chronic can be treated by the compositions and methods described herein.

The agent that promotes or stimulates C3aR and/or C5aR signaling can also be provided in or on a surface of a medical device used to treat an internal and/or external wound. The medical device can comprise any instrument, implement, machine, contrivance, implant, or other similar or related article, including a component or part, or accessory, which is, for example, recognized in the official U.S. National Formulary, the U.S. Pharmacopoeia, or any supplement thereof; is intended for use in the diagnosis of disease or other conditions, or in the cure, mitigation, treatment, or prevention of disease, in humans or in other animals; or, is intended to affect the structure or any function of the body of humans or other animals, and which does not achieve any of its primary intended purposes through chemical action within or on the body of man or other animals, and which is not dependent upon being metabolized for the achievement of any of its primary intended purposes.

The medical device can include, for example, endovascular medical devices, such as intracoronary medical devices. The medical device may additionally include either implantable pacemakers or defibrillators, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, cardiac valves, and tissue engineered constructs, such as bone grafts and skin grafts.

In other embodiments, the agent that promotes or stimulates C3aR and/or C5aR signaling of the cells can be administered in combination with a growth factor that promotes wound repair and/or mitigates apoptosis of cells of the wound. The growth factor can include, for example, VEGF, NGF, GM-SCF, EGF, FGF, IGF, BDNF, BMP, SDF-1, and/or HGF.

The following examples are for the purpose of illustration only and are not intended to limit the scope of the claims, which are appended hereto.

Example 1

Complement has been shown to be an important component in various pathological responses involving ECs, in all cases the effects have been attributed to serum complement. We tested whether autocrine GPCR signal transduction might be connected with the anti-apoptotic and/or mitotic effects of VEGF on ECs.
Materials and Methods
Reagents and Antibodies VEGF-A was from Prospect (Ness Ziona, Israel). C3aR antagonist (C3aR-A) and C5aR antagonist (C5aR-A) are from Merck (Darmstadt, Germany). Anti-C3 and Anti-05 was purchased from BD PharMingen (San Diego, Calif.). Anti-C3aR and Anti-05aR were purchased from Santa Cruz Biotech (Santa Cruz, Calif.). Endothelial cell growth supplement was purchased from BD Biosciences (San Diego, Calif.). Anti-phospho-VEGFR2 (pYpY1054/1059) was purchased from Invitrogen (Camarillo, Calif.).
Cells & the Isolation of Primary Aortic ECs bEnd.3 cells and MS1 murine EC lines were cultured in 10% and 5% FBS, respectively with DMEM. The primary mouse aorta endothelial cells (MAECs) were isolated from wild-type C57BL/6J mice (WT), Daf1$^{-/-}$, C3aR$^{-/-}$C5aR$^{-/-}$ at ages from 1 to 4 months, by utilizing a non-mechanical and non-enzymatic method. The outgrowth of endothelial cells from aortic rings was markedly facilitated within first 72 h in the absence of antibiotics. Aortic rings thus were discarded at culture day 3 to avoid the possible contamination of non-endothelial cell types. After removing the aortic rings, cells were maintained in completed DMEM/F12 medium consisting of 20% FBS, 2 mM L-glutamine, 1 nonessential amino acid, 0.05 mg/ml endothelial cell growth supplement (ECGS), 100 units/ml penicillin, 100 g/ml streptomycin, and 0.1 mg/ml heparin until confluent.
Gene Expression and Flow Cytometry RNA was isolated by the TRIzol method (Invitrogen). Reverse transcription was achieved with Superscript-III reverse transcriptase (Invitrogen) using supplied oligo dT primers. qPCR was performed in a 24 µl volume with SYBR Green PCR mix (Applied Biosystems) using gene specific qPCR primers.

For C3aR and C5aR staining cells were harvested after plating in 10% FBS supplemented DMEM via Versene (Invitrogen) and stained by using three-layer immunoenzyme method. Stained cells were analyzed on a Becton Dickinson LSRII.
Quantitation of Cell Growth For studies with bEnd.3 and MS-1 cells, $5 \times 10^4$ cells were plated in 24-well plates and allowed to adhere for 24 hr. Following culturing in 0.5% FBS with DMEM for another 24 hours, the cells were treated as described in the FIG. legends. Growth was quantified manually at 24, 48 and 72 hr with trypan blue. At least 95% of cells were viable in all experiments. VEGF-A was used at a concentration of 30 ng/ml, C3a and C5a at 1 ug/ml, and anti-C3 and ant-C3 mAbs at I ug/ml.
C3a/C5a/VEGF ELISAs and Propidium Iodide Staining Enzyme-linked immune-adsorbent assays were conducted to quantify C3a and C5a levels in culture supernatants. Ninety six well plates were used and the manufacturer's (eBioscience) protocol followed. FACS without sodium azide was used for diluents with blocking buffer and color was developed using enhanced TMB solution with $H_2O_2$. The stop solution consisted of 2 N $H_2SO_4$.

Propidium iodide staining was performed as described previously (ref). In brief, the cells were serum starved for 24 hrs followed by administration of 1 µM colchicine (Sigma). 16 hrs following colchicine treatment, cells were given either growth factor treatment or 17 ng/mL mC5a. After an additional 24 hrs, cells were removed from plating via Trypsin/EDTA and fixed in 0.25% Formaldehyde for 10 mins at 37° C. Cells were spun out of formaldehyde solution and resuspended in 90% methanol at 4° C. until assayed. Following removal from methanol, excess RNA was removed via treatment with RNase (Sigma) and stained with propidium iodide for 30 mins at 4° C. Cells were analyzed on an Epics XL.
Hypoxia and 2-D HUVEC Tube Formation The mitochondrial uncoupler protonophore carbonyl cyanide p-(trifluoromethoxy)phenylhydrazone (FCCP)+iodoacetate (IAA), which simulate hypoxia when added to cells, was incubated for 1 hr and 2 hr with HUVEC, and C3, fB, and fD mRNA levels were assayed by qPCR.

Fifty µL of the growth factor reduced matrigel (BD Biosciences) was allowed to polymerize in 96-well plate at 37° C. for 30 minutes. Triplicates of 25,000 HUVEC were plated onto the prepared matrigel in a volume of 150 µL of EBM-2 media (Lonza) in four different conditions: no growth factors, 30 ng/ml of VEGF, 30 ng/ml of VEGF and with 15 ng/ml each of C3aR-A and C5aR-A and the complete set of factors. After approximately 15 hr, images were captured using a light microscope in high magnification.
Corneal Neovascularization and Tumor Angiogenesis Model Corneal neovascularization was induced in 6-8 wk-old (C57BL/6) WT, Daf1$^{-/-}$, C3aR$^{-/-}$C5aR$^{-/-}$, and Daf1$^{-/-}$ C3aR$^{-/-}$C5aR$^{-/-}$ mice (n=5 each group) by placing a non-penetrating suture (0-11 Nylon, Alcon Inc.) in the center of the cornea under a dissecting microscope. On days 7, 9, 11, and 15, corneal vessels were examined after intravenous administration of 100 µl of 2.5% fluorescein-dextran (Sigma) by fluorescence microscopy. The protocol was approved by the Case Western Reserve University Institutional Animal Care and Use Center (IACUC). Male mice were injected subcutaneously with $1.5 \times 10^6$ RM1 prostate cancer cells. Tumors were collected 10 days after injection and were weighed, photographed, snap-frozen in OCT and processed for immunohistochemical staining with biotin-conjugated rat anti-mouse CD31 antibody (BD Biosciences, San Jose, Calif.). Stained sections were analyzed using fluorescent or bright field imaging microscopy (Leica, Germany) and ImagePro Plus Capture and Analysis software version 6.1 (Media Cybernetics). CD31-positive areas were quantified in 5-10 independent fields per tumor implant.

Results

ECS Locally Synthesize Complement, C3a/C5a are Generated from this Local Synthesis, and Autocrine Interactions of these Anaphylatoxins with C3aR/C5aR on ECs are Essential to Sustain EC Viability.

Figure 4:
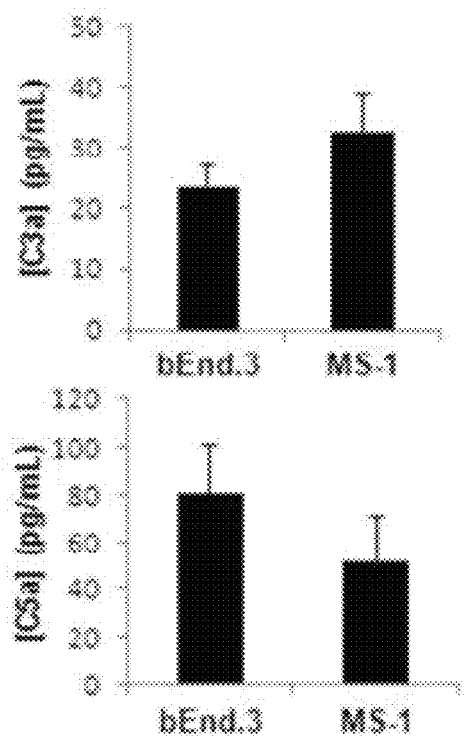
FIG. 4 illustrates a chart showing autocrine C3aR/C5aR signaling is essential for EC viability. bEnd.3 and MS-1 cells were incubated for 24 hours in EC growth medium, and locally produced C3a and C5a in culture supernatants quantitated by ELISA.
Figure 5:
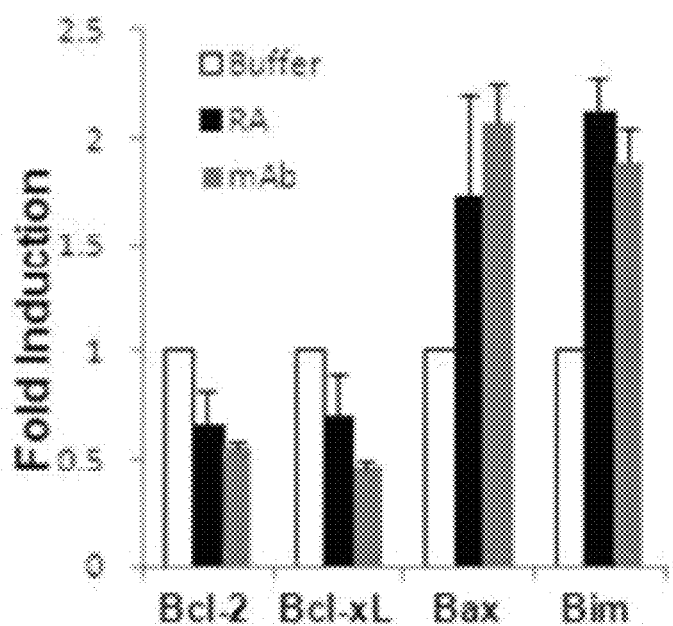
FIG. 5 illustrates a chart showing Bcl-2, Bclx-L, Bax, and Bim mRNA expression levels in bEnd.3 cells incubated for 8 hr with C3aR-A/C5aR-A (10 ng/ml each) or anti-C3a/C5a (1 ug/ml each).
Figure 6:
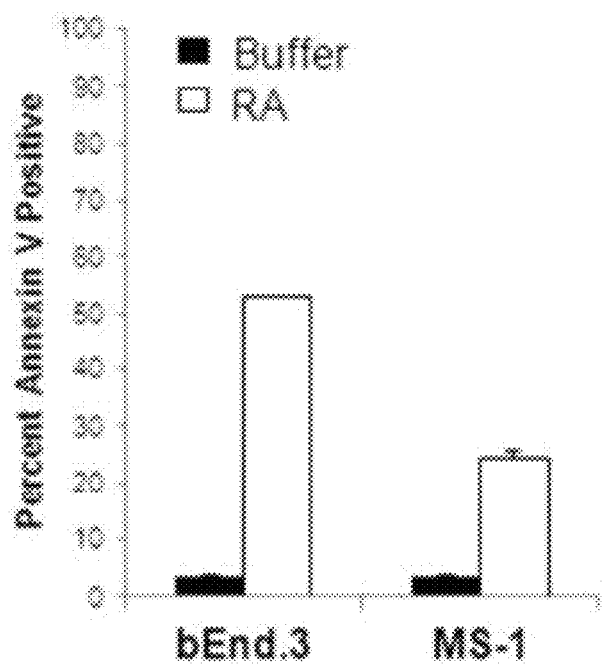
FIG. 6 illustrates a chart showing Annexin V positivity of bEnd.3 cells and MS-1 cells administered C3aR-A/C5aR-A (10 ng/ml each).

As a first test of whether ECs, like CD4+ tonically synthesize complement (under homeostatic conditions) and whether this local synthesis leads to autocrine C3aR/C5aR signaling in ECs, we examined serum free cultures of bEnd.3 and MS-1 murine EC cell lines for local C3a/C5a production and for surface expression of C3aR/C5aR. The culture supernatants of both EC lines contained C3a and C5a and both EC lines expressed both GPCRs (FIG. 4) To test whether tonic C3aR/C5aR signaling provides survival signals to ECs as found for CD4+ cells, we added pharmacological C3aR/C5aR antagonists (C3aR-A/C5aR-A) or with anti-C3a/C5a mAbs specific for neo-epitopes in the C3a/C5a ligands (not present on the parental C3/C5 proteins) to the serum free cultures and assayed for markers of apoptosis. Blockade of either the receptors or their ligands evoked surface Fas/FasL expression, caused decreased intracellular Bcl-2/Bcl-x2 and increased Bax/Bim mRNAs, and rendered the ECs susceptible to Annexin V binding (FIGS. 5-6). The effects of the C3aR/C5aR blockade on Bcl-2 mRNA expression in ECs simulated that of blockade of VEGFR2 signaling.

Figure 7:
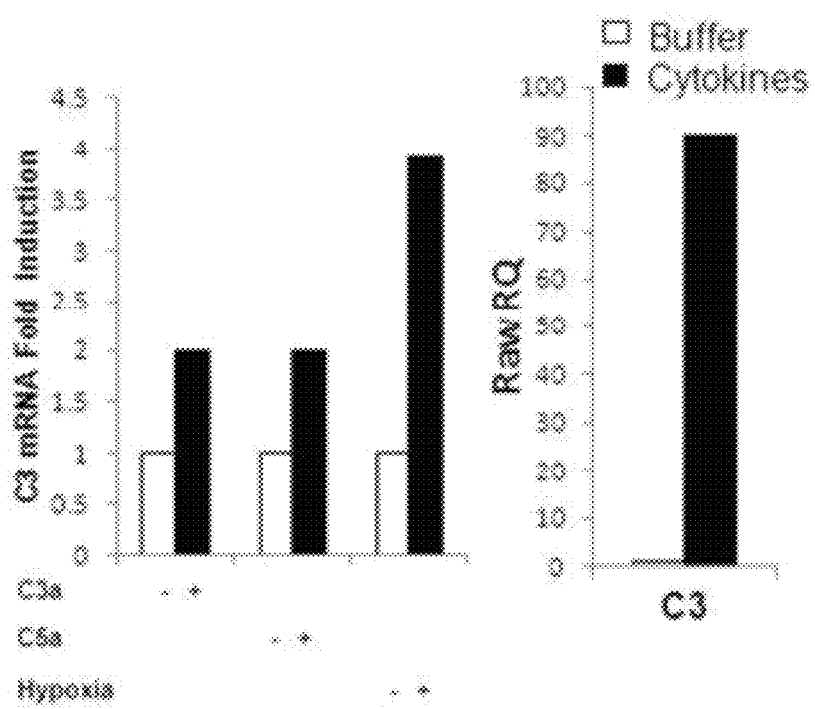
FIG. 7 illustrates a chart showing complement mRNA transcription (Left, data shown for C3 mRNA) in HUVEC cells following C3a or C5a administration or hypoxia. Hypoxia was induced by FCCP and IAA in HUVEC for 1 hr and C3 mRNA levels were quantified by qPCR (Right).
Figure 8:
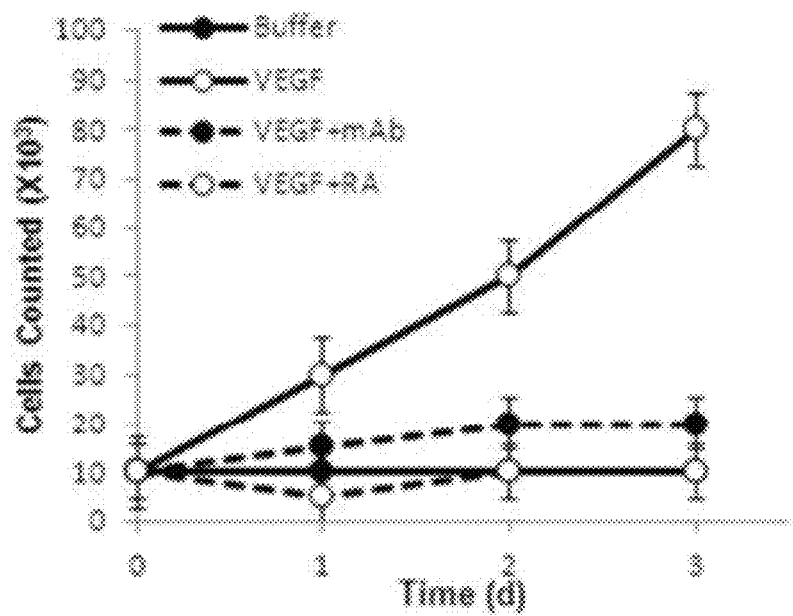
FIG. 8 illustrates plots showing growth of bEnd.3 cells following administration of C3aR-A/C5aR-A signaling and/or VEGF.

We next conversely assessed how transducing C3aR/C5aR signals into ECs affects endogenous EC complement production and whether it is connected with "classical" EC responses. We incubated HUVEC with 1) inflammatory cytokines, 2) the mitochondrial uncoupler protonophore carbonyl cyanide p-(trifluoromethoxy)phenylhydrazone (FCCP)+iodoacetate (IAA) (which mimics hypoxia), or 3) C3a or C5a, after which we assayed complement mRNA transcripts by qPCR. The mitochondrial uncoupler evoked an increase in complement transcripts consistent with this signal transduction functioning to amplify EC growth and prevent apoptosis in response to hypoxia (FIG. 7). Added IL-1/IFN-γ/TNF-α had the same effect (FIG. 7). Both added C3a and added C5a increased transcription of C3, indicative of the ability of both anaphylatoxins to establish auto-inductive signaling loops (FIG. 8).

VEGF Growth Induction Depends on C3aR/C5aR Signaling.

Figure 9:
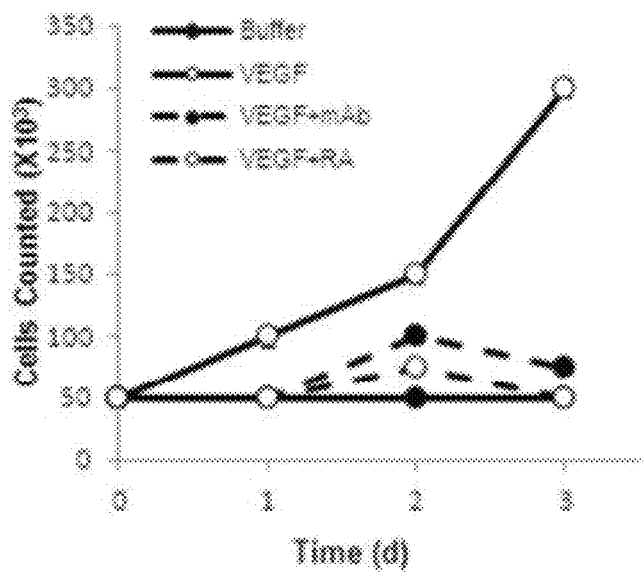
FIG. 9 illustrates plots showing growth of MS-1 cells following administration of C3aR-A/C5aR-A signaling and/or VEGF.
Figure 10:
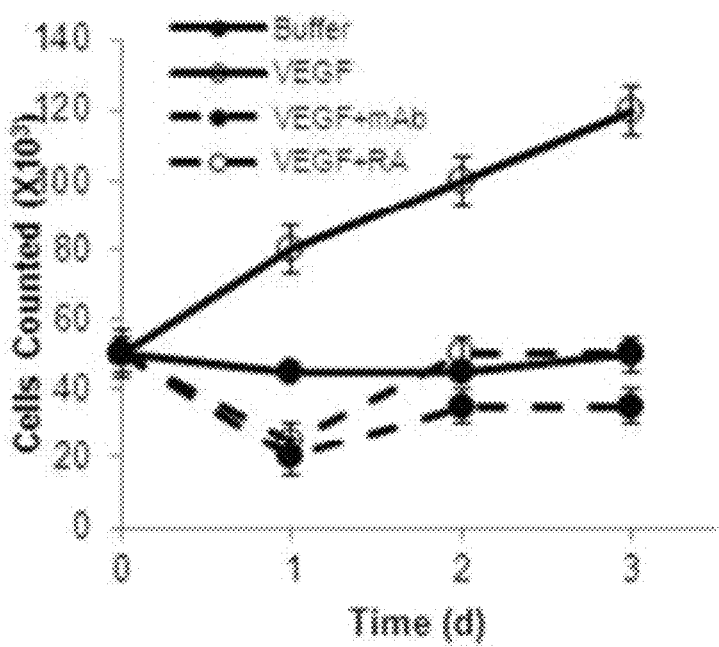
FIG. 10 illustrates plots showing growth of HUVECs incubated with C3aR-A/C5aR-A (10 ng/ml each) or anti-C3/anti-C5 mAbs (1 μg/ml each) at 24, 28 and 72 hr assayed.
Figure 11:
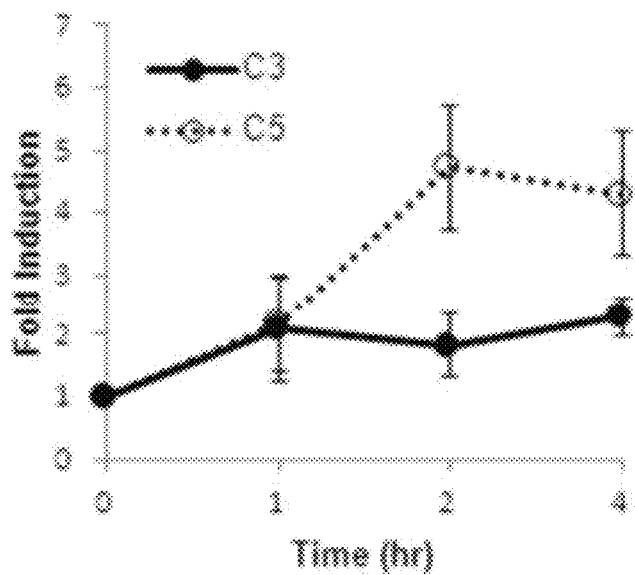
FIG. 11 illustrates plots showing expression of C3 and C5 mRNA of bEnd.3 cells incubated for 1 hr with VEGF-A (30 ng/ml).
Figure 12:
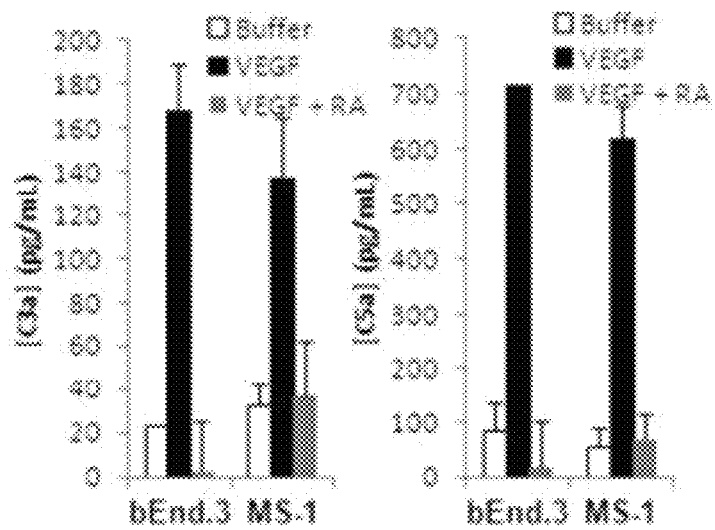
FIG. 12 illustrates a chart showing C3a/C5a production of bEnd.3 cell or MS-1 cells treated with VEGF and C3aR-A/C5aR-A.

As a first test of whether VEGF growth induction and autocrine C3aR/C5aR signaling in ECs are mechanistically connected, we added VEGF-A to serum starved MS-1 and bEnd.3 cells in the absence or presence of C3aR-A/C5aR-A or anti C3a/C5a mAbs and counted cell numbers over 72 hr. Blockade of either the receptors or their C3a/C5a ligands abolished VEGF-A induced proliferation of both EC lines (FIGS. 8-9). A similar effect was observed in HUVEC cultures (FIG. 10). Blockade of the individual receptors or ligands individually (data not shown) inhibited VEGF-A induced growth and that blockade of both synergized in the inhibition. C3aR/C5aR antagonism or C3a/C5a neutralization did not affect the growth of CTLL cells which is IL-2 dependent and only partially inhibited that of MS-1 or bEnd.3 in 10% plasma verifying that the inhibitory effects on VEGF-A growth induction were specific rather toxic effects on the cells. To determine whether VEGF growth induction is interconnected with upregulated C3aR/C5aR signaling, we examined the effect of added VEGF-A on local complement production by MS-1 and bEnd.3 cells. qPCR of cell extracts and ELISAs of their culture supernatants showed that VEGF-A both up-regulated C3/C5 mRNA transcripts and increased local C3a/C5a production (FIGS. 11-12). These findings show that amplified C3aR/C5aR GPCR signals integrate with VEGF growth signals.

Because the disruptive effect of C3aR/C5aR antagonism on VEGF growth induction could be a consequence of the requirement of autocrine C3aR/C5aR signaling for EC viability, we performed cell cycle assays. Adding C5a to serum starved HUVEC caused transition from G0 into G2 identically to adding VEGF-A. Moreover, C3aR/C5aR blockade prevented VEGF-A triggering of the cell cycle. These findings that autocrine C3aR/C5aR signaling not only prevents EC apoptosis but drives EC growth point to a bidirectional signaling mechanism wherein C3aR/C5aR GPCR signaling transactivates to VEGFR2 signaling and vice versa.

C3aR/C5aR Signals are Required for VEGF Induced Growth of ECs.

Figure 13:
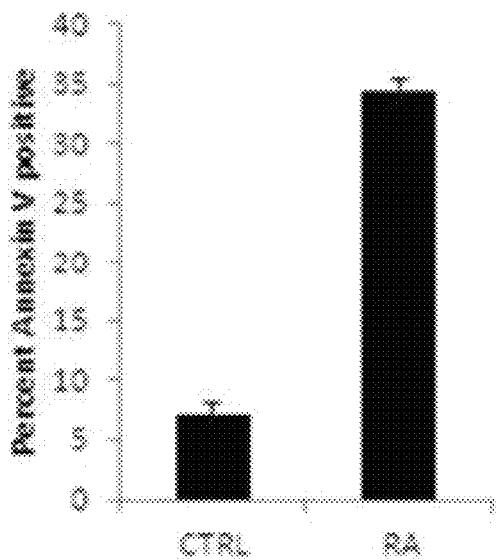
FIG. 13 illustrates a chart showing Annexin V positivity in primary ECs added of C3aR-A/C5aR-A (10 ng/ml each).
Figure 14:
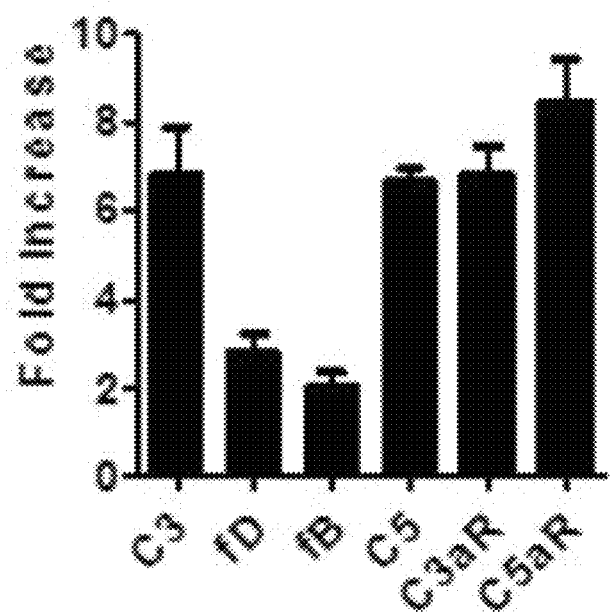
FIG. 14 illustrates a chart showing C3, fB, fD, C5, C3aR, and C5aR levels of primary ECs were incubated for 30 min with VEGF-A (30 ng/ml).
Figure 15:
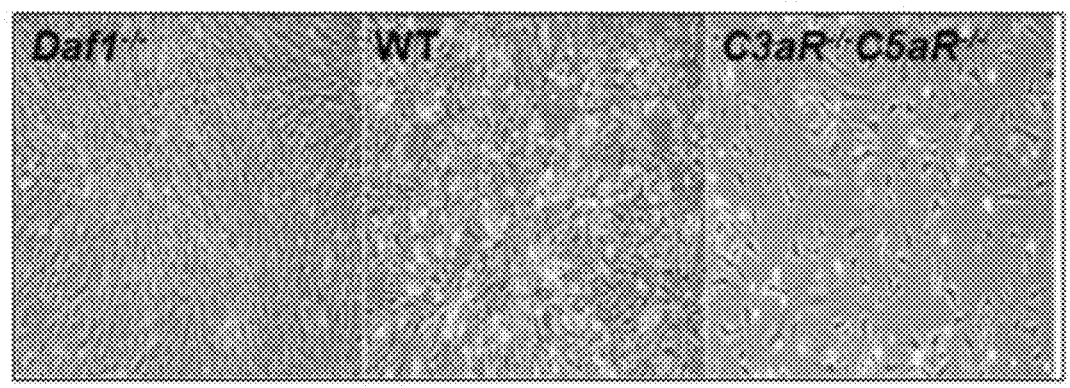
FIG. 15 illustrates images showing primary ECs isolated from aortic rings of Daf1$^{-/-}$, WT and C3aR$^{-/-}$C5aR$^{-/-}$ mice grown in EC growth medium for 2 wk and photographed following the first passage.
Figure 16:
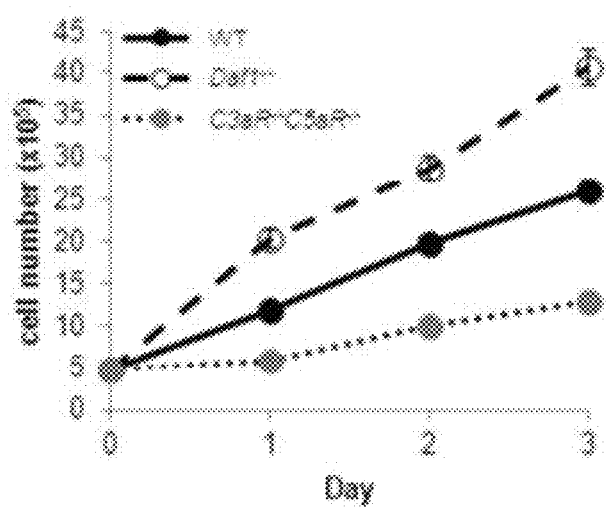
FIG. 16 illustrates a plot showing cell numbers of 5×10$^5$ ECs of each genotype cultured in EC growth medium after 24, 48, and 72 hr.
Figure 17:
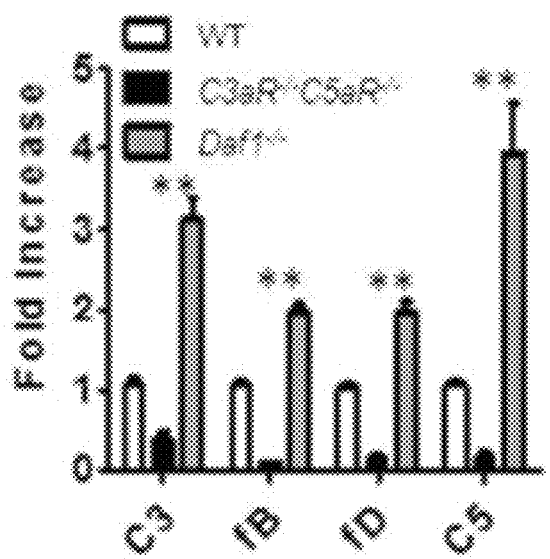
FIG. 17 illustrates a chart showing mRNA expression of C3, fB, fD, and C5 by cells from whole aorta of each identified genotype.
Figure 18:
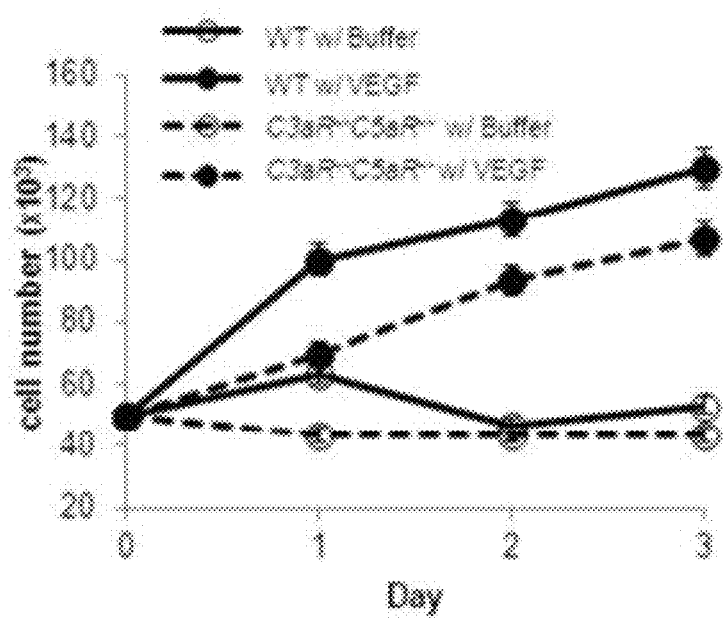
FIG. 18 illustrates plots showing growth of WT and C3aR$^{-/-}$C5aR$^{-/-}$ incubated with VEGF-A (30 ng/ml) at 24, 48, and 72 hr assayed.

To validate that the above findings apply physiologically, we prepared primary ECs from aortas of WT mice. As found for the bEND.3 and MS-1 EC lines and for HUVEC, aortic ECs from WT mice expressed C3aR and C5aR, antagonizing C3aR/C5aR signaling induced markers of apoptosis (FIG. 13), and VEGF-A upregulated mRNA transcripts of all of the components/receptors associated with autocrine C3aR/C5aR signaling (FIG. 14). We similarly prepared aortic ECs from mice in which C3aR/C5aR signaling is potentiated (Daf1$^{-/-}$ mice) or C3aR and C5aR are deleted (C3aR$^{-/-}$C5aR$^{-/-}$ mice). Side by side comparisons of the growth rates of the Daf1$^{-/-}$ and C3aR$^{-/-}$C5aR$^{-/-}$ aortic ECs to that of WT aortic ECs (FIG. 15) showed that the absence of DAF favored EC proliferation (1.77±0.06 vs 1.30±0.017× $10^5$ cells 24 hr after plating $10^5$ cells) whereas the absence of C3aR/C5aR virtually abolished it (1.07±0.05×$10^5$ cells). Quantitative studies in which we cultured 5×$10^4$ ECs from the three genotypes over a 72 hr period and counted cell numbers documented an ~2-fold faster growth (2×$10^6$±0.15 vs 4×$10^6$±0.017 p<0.005) of Daf1$^{-/-}$ ECs than of WT ECs (consistent with potentiated C3aR/C5aR signaling), and little or no growth (2×$10^6$±0.15 vs 1×$10^6$±0.05p<0.005) of C3aR$^{-/-}$C5aR$^{-/-}$ ECs (consistent with precluded C3aR/C5aR signaling) (FIG. 16). To establish if the differences in growth rates correlate with differences in EC complement production in vivo, we assayed perfused aortas from Daf1$^{-/-}$, WT, and C3aR$^{-/-}$C5aR$^{-/-}$ mice for mRNA transcripts of complement components connected with C3aR/C5aR signaling. qPCR assays documented upregulated and suppressed C3/fB/fD/C5 mRNA transcripts in Daf1$^{-/-}$ and C3aR$^{-/-}$C5aR$^{-/-}$ aortas, respectively (FIG. 17). To study how the absence of C3aR/C5aR signaling affects VEGF growth induction, we serum starved aortic ECs from WT and C3aR$^{-/-}$C5aR$^{-/-}$ mice and added VEGF-A to cultures. The genetic absence of C3aR/C5aR markedly suppressed VEGF induced growth (FIG. 18). However, unlike the virtual abrogating effects of disrupted C3aR/C5aR signaling in WT ECs with the antagonists or mAbs, VEGF-A retained some growth inductive capacity, an issue that will addressed below.

C3aR/C5aR Signaling in ECs is Essential for Vascular Tube Formation and for Angiogenesis in Vivo.

Figure 19:
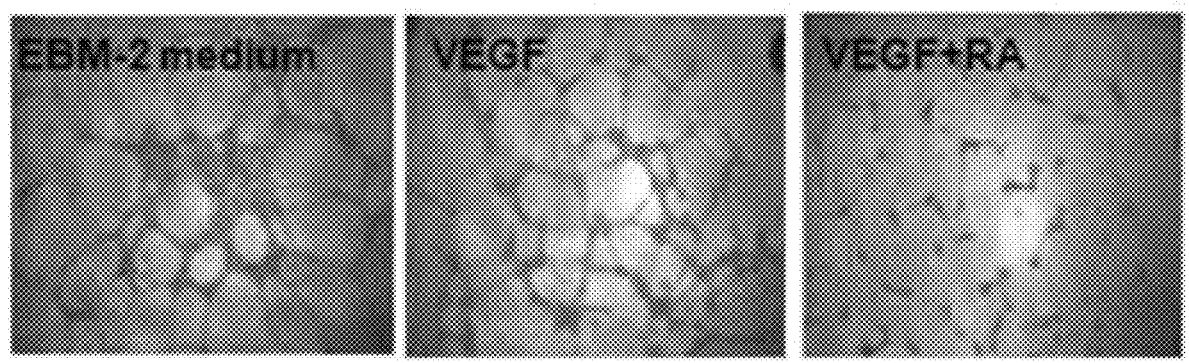
FIG. 19 illustrates images showing autocrine C3aR/C5aR signaling in ECs is essential for HUVEC tube formation and corneal neovascularization. HUVEC were plated with EBM-2 Basal Medium without supplemental growth factors, with VEGF-A, or with VEGF-A plus C3aR-A/C5aR-A.

As a first test of whether the above connection of VEGF growth induction with autocrine C3aR/C5aR signaling is physiologically relevant, we performed two-dimensional tube formation assays with HUVEC to determine how this GPCR signaling affects angiogenesis. Culturing HUVEC under conventional conditions with EBM-2 basal medium containing supplemental growth factors yielded the typical growth pattern of an EC tubal network consisting of cluster regions with a few branches. (FIG. 19, Left). Substitution of exogenous VEGF for the growth factor cocktail evoked increased branch points (FIG. 19, Middle). In contrast, the inclusion of C3aR-A/C5aR-A together with VEGF-A under identical conditions essentially disrupted tube formation (FIG. 19, Right).

To establish whether in vivo angiogenesis, in fact, depends on C3aR/C5aR signaling, we used two in vivo models. In the first model, we placed non-penetrating sutures in the corneas of WT, Daf1$^{-/-}$, C3aR$^{-/-}$C5aR$^{-/-}$ and Daf1$^{-/-}$C3aR$^{-/-}$C5aR$^{-/-}$ mice. This assay has the advantage of measuring neo-angiogenesis (new blood vessel growth) since the cornea is normally avascular. Beginning at day 5, we examined corneas by fluorescence confocal microscopy after intravenously administering fluorescent dextran beads. In contrast to the gradual influx of blood vessels at the corneal margins starting at day 9 in WT mice, markedly accelerated and more robust influx occurred in Daf1$^{-/-}$ mice, and virtually none occurred in C3aR$^{-/-}$C5aR$^{-/-}$ or Daf1$^{-/-}$C3aR$^{-/-}$C5aR$^{-/-}$ mice.

Figure 20:
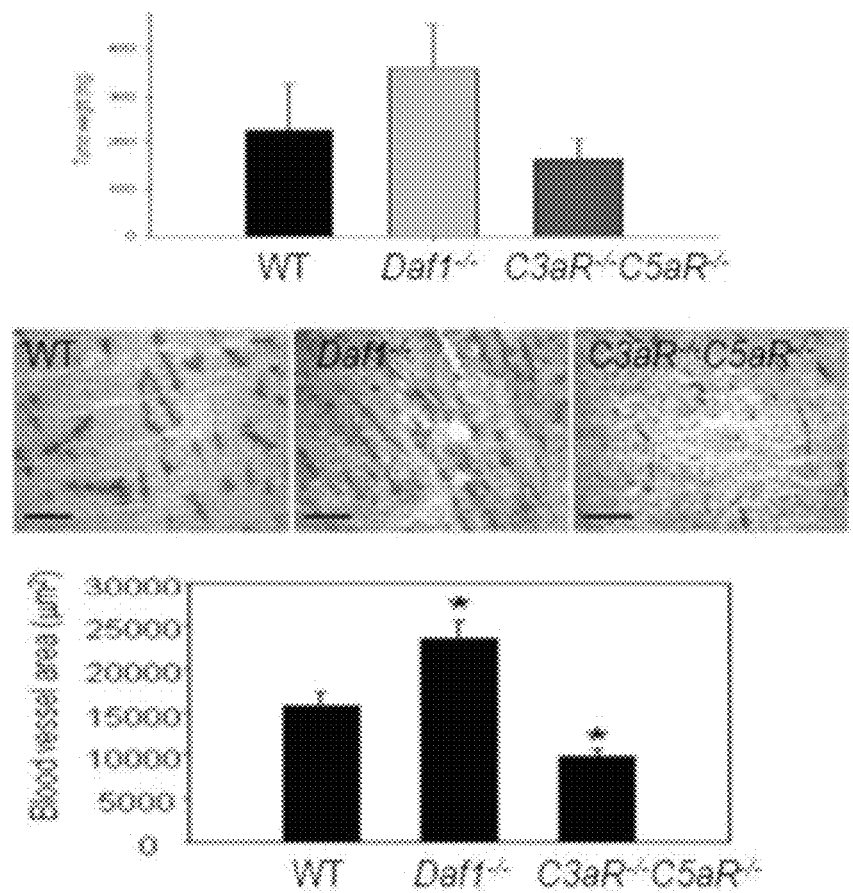
FIG. 20 illustrates images showing male mice were injected subcutaneously with 1×10$^6$ RM1 prostate cancer cells. Tumors were collected 10 days after injection and were weighed (Top, n=8). Representative images of immunostaining for CD31 in tumor sections of WT, Daf1$^{-/-}$, and C3aR$^{-/-}$C5aR$^{-/-}$ mice, showing CD31 expression in new vessels (Middle). CD31-positive areas were quantified in 5-10 independent fields per tumor implant (Bottom).

In the second model, we implanted RM1 prostate tumors which are highly vascularized and dependent on angiogenesis for their progression (Huang et al., 2005) into the flanks of male WT, Daf1$^{-/-}$ and C3aR$^{-/-}$C5aR$^{-/-}$ mice. We harvested the tumors at day 14 post inoculation, weighed them, and immunohistochemically examined sections of their stroma staining for the EC marker CD31. The tumors in C3aR$^{-/-}$C5aR$^{-/-}$ mice were smaller (227.93±201.28 vs 164.33±89.7, p=0.29) than in WT mice, and larger (227.93±201.28 vs 359±185.31, p=0.18) than in Daf1$^{-/-}$ mice (FIG. 20, Top). The sections showed significantly reduced vessel density and vascular area in tumors grown in C3aR$^{-/-}$C5aR$^{-/-}$ mice compared to WT mice (9772±799 vs. 15699±1591 μm$^2$, P=0.004, n=8) (FIG. 20, Bottom). In contrast, angiogenesis was significantly enhanced in tumors from Daf1$^{-/-}$ mice (23458±1976 vs. 15699±1591 μm$^2$, P=0.01, n=8).

C3aR/C5aR Signaling is Essential for VEGFR2 Phosphorylation

Figure 21:
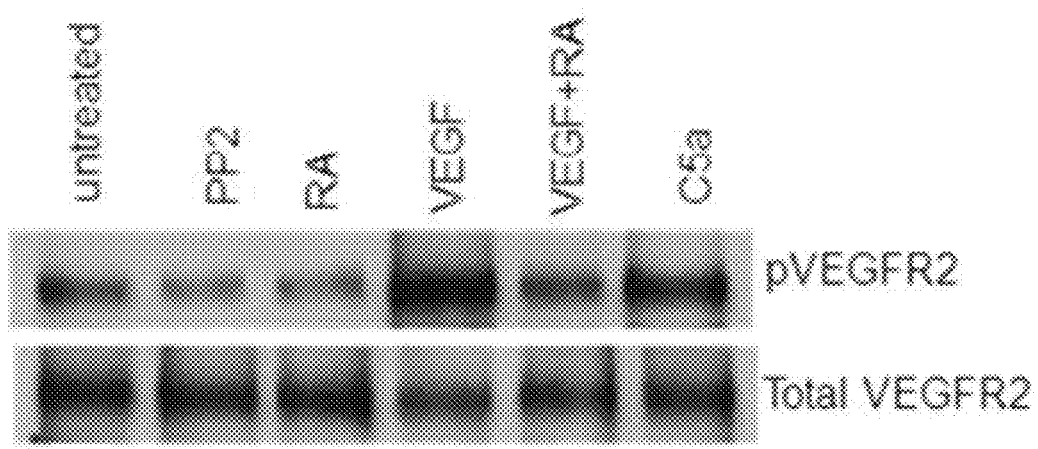
FIG. 21 illustrates an immunoblot of VEGFR2 phosphorylation. C5a or VEGF-A was added to serum starved primary cultures of WT murine ECs in the absence or presence of C3aR-A/C5aR-A and VEGFR2 phosphorylation assessed by immunoblotting with anti p-T1094/T1095 mAb.
Figure 22:
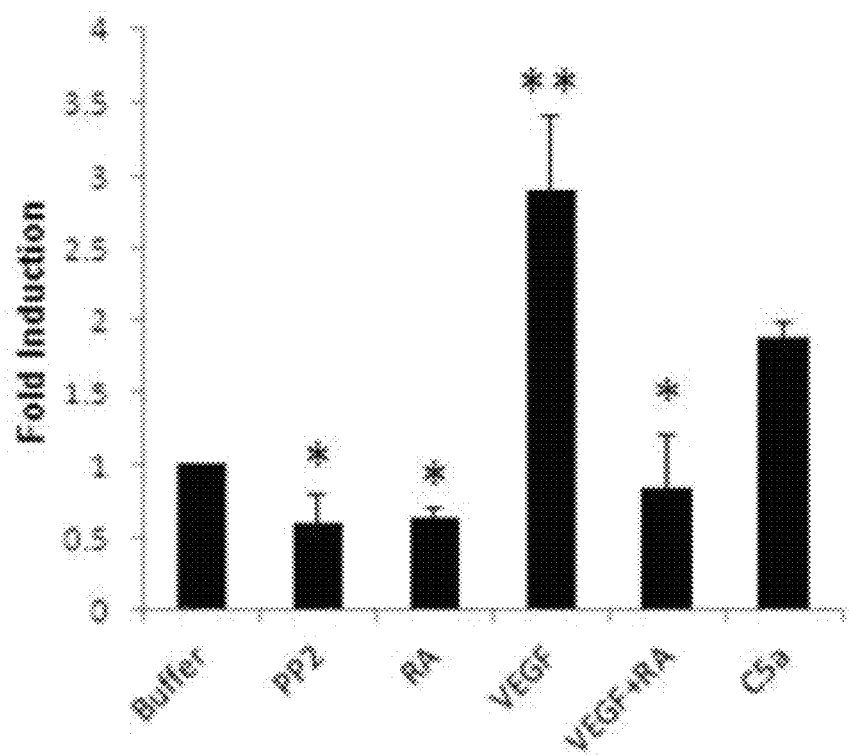
FIG. 22 illustrates a chart showing quantitation of bands in FIG. 21.

To directly establish whether C3aR/C5aR signaling is integral to VEGF signaling, we next evaluated phosphorylation of VEGFR2. We tested 1) how adding C5a to primary WT ECs affects VEGFR2 autophosphorylation and 2) whether VEGFR2 phosphorylation induced by added VEGF-A is affected by antagonizing C3aR/C5aR signaling. We incubated serum starved WT aortic ECs with C5a or with VEGF-A in the absence or presence of C3aR-A/C5aR-A, after which we probed immunoblots of protein lysates and anti-pVEGFR2$^{Y1054/1059}$ mAb or pan VEGFR2 antibody. The added C5a increased VEGFR2$^{Y1054/1059}$ phosphorylation relative to untreated controls and the C3aR/C5aR blockade virtually abolished VEGF-A induced VEGFR2 auto-phosphorylation (FIG. 21-22).

Figure 23:
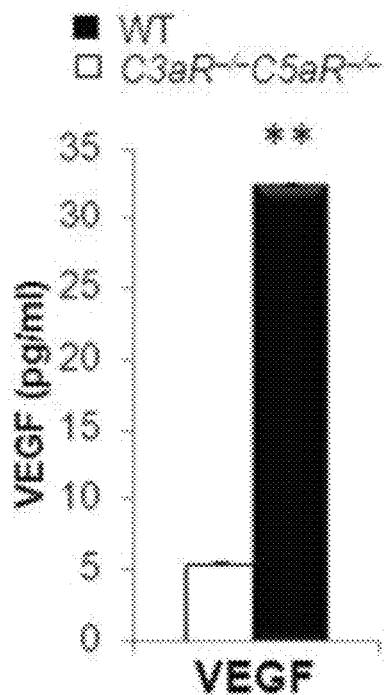
FIG. 23 illustrates a plot showing the expression of VEGF from the second passage of primary ECs from WT and C3aR$^{-/-}$C5aR$-/-$.
Figure 24:
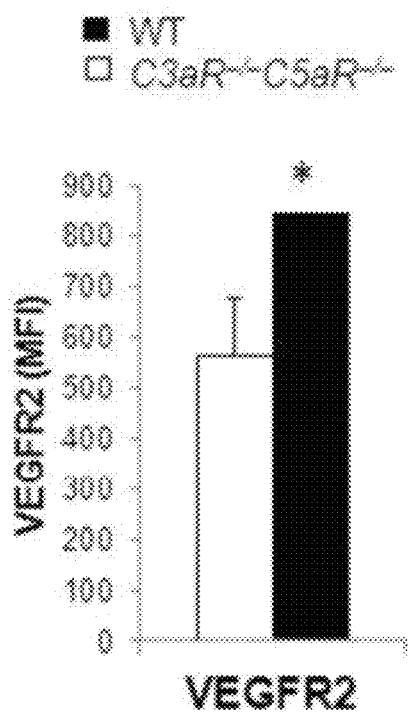
FIG. 24 illustrates the expression of VEGFR2 of primary ECs starved in DMEM/F12 with 0.5% FBS for 24 hrs. The supernatants and cell lysates were collected and analyzed for VEGF content by ELISA. The results were normalized by protein concentration.
Figure 25:
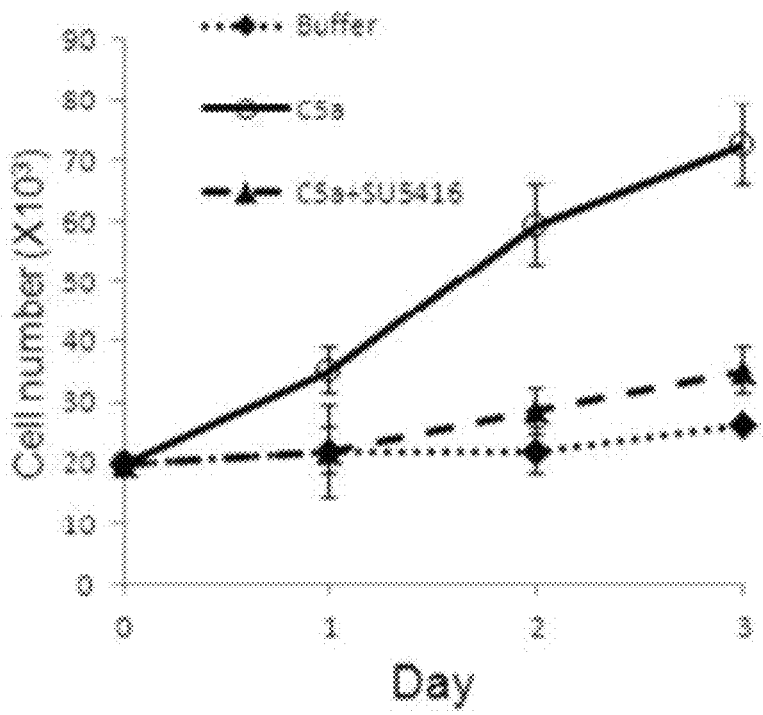
FIG. 25 illustrates plots showing growth of serum starve primary cultures of WT murine ECs in the absence or presence of SU5416 or C5a. The cell proliferation was quantified by Trypan blue exclusion.
Figure 26:
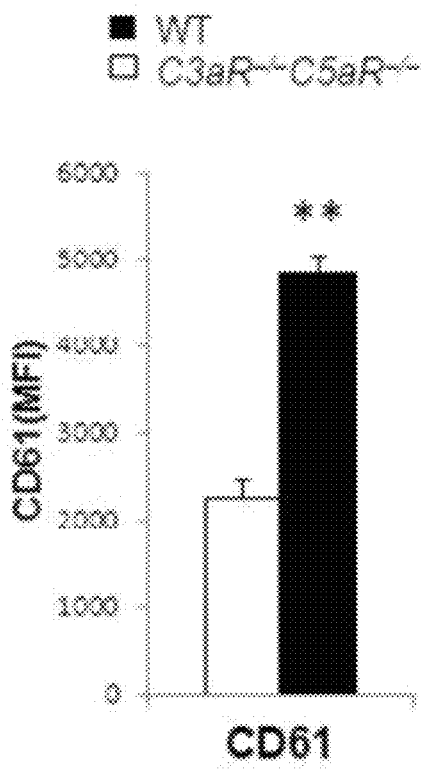
FIG. 26 illustrates a chart showing the expression of Integrinβ3 from the passage 3-4 of primary EC of WT and C3aR$^{-/-}$C5aR$^{-/-}$ measured by FACS.

Up-Regulation of VEGFR2 and Endogenous VEGF-A Production Compensates for Pro-Apoptotic Signaling in C3aR-/-C5aR-/- ECs The above experiments with WT ECs in this Example showed that autocrine C3aR/C5aR signaling provides survival signals and that blockade of this signaling triggers both the intrinsic and extrinsic PCD pathways. We compared VEGFR2 expression levels and endogenous VEGF-A production in C3aR$^{-/-}$C5aR$^{-/-}$ and WT ECs. ELISAs of their supernatants of untreated the C3aR$^{-/-}$C5aR$^{-/-}$ ECs (FIG. 23) showed 5-fold more VEGF-A production compared to WT ECs, and flow cytometry (FIG. 24) showed 2-fold increased levels of VEGFR2 on their surfaces. Addition of the VEGFR2 inhibitor SU5416 to cultures of C3aR$^{-/-}$C5aR$^{-/-}$ ECs without or with added C5a (FIG. 25) abolished their growth, indicating that upregulated VEGFR2 auto-phosphorylation compensated for the loss of C3aR/C5aR signaling in the knockouts and that EC viability depended entirely on this compensation. Because β3 Integrin (CD61) has been reported to be regulated by VEGFR2 signaling and implicated in EC survival signaling, we compared CD61 expression in C3aR$^{-/-}$C5aR$^{-/-}$ and WT ECs. Flow cytometry analysis of C3aR$^{-/-}$C5aR$^{-/-}$ ECs showed 2.5-fold increased CD61 levels (FIG. 26).

VEGF Induces C3aR/C5aR Signaling by an IL-6 and Stat3 Dependent Mechanism

Figure 27:
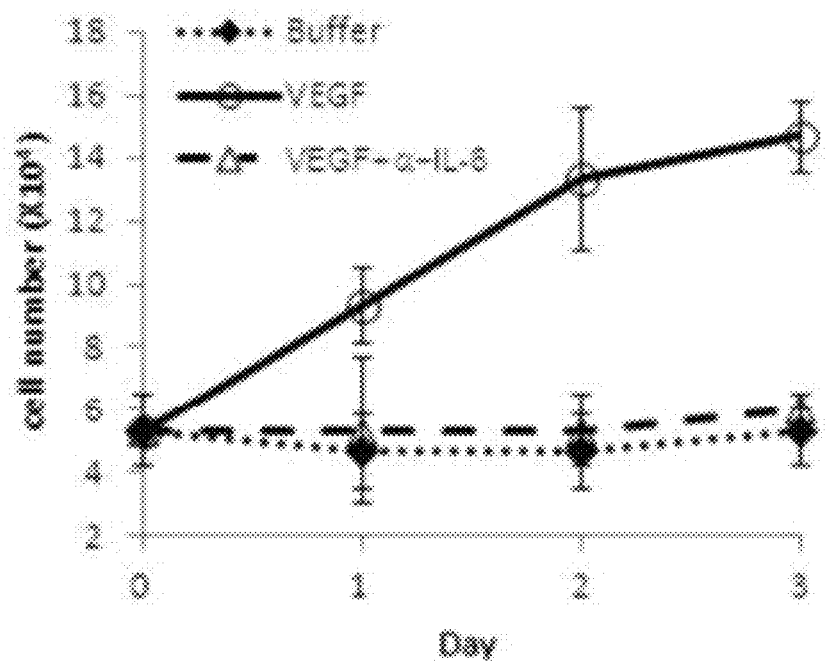
FIG. 27 illustrates plots showing the growth of ECs in response to VEGF induces C3aR/C5aR signaling via an IL-6 and Stat3 dependent mechanism. VEGF-A was added to serum starved MS-1 cells in the absence or presence of anti-IL-6 neutralizing mAb (2 μg/ml) and growth was quantified at 24, 28 and 72 hr.
Figure 28:
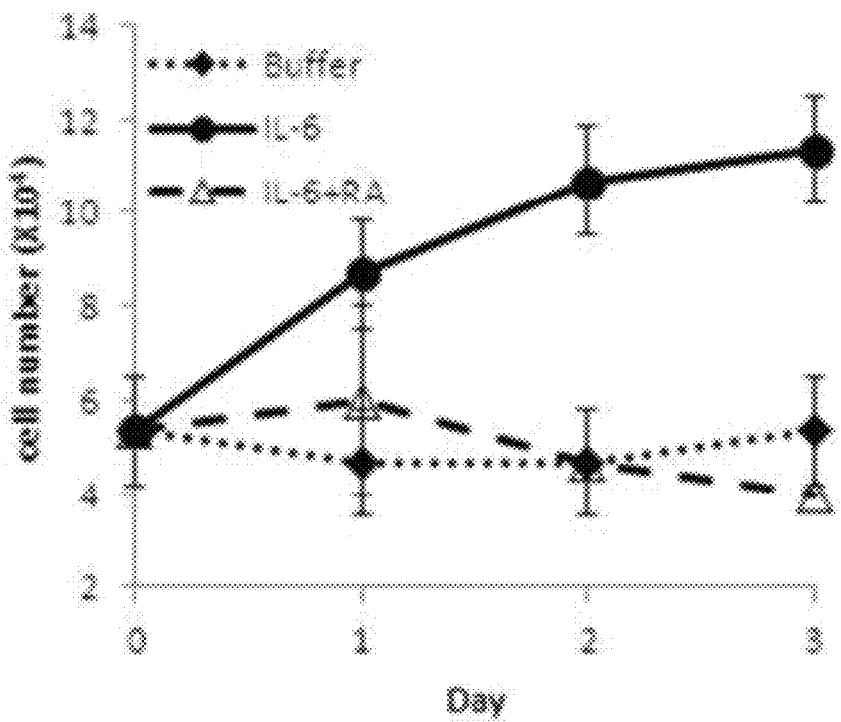
FIG. 28 illustrates plots showing the growth of serum starved MS-1 cells in the absence or presence of C3aR-A/C5aR-A (10 ng/ml each) and IL-6 (10 ng/ml) at 24, 48 and 72 hr.

While the experiments above showed that C3aR/C5aR signaling transactivates to phosphorylate VEGFR2, they left unanswered how VEGFR2 signaling is mechanistically linked to C3aR/C5aR signaling. Numerous past studies have linked VEGF with both IL-6 and p-Stat3 our prior studies by ourselves has shown that C5a induces IL-6 and that IL-6 signaling is interconnected with C3aR/C5aR signaling. To determine if the linkage between VEGF and C3aR/C5aR signaling in ECs involves IL-6, we incubated MS-1 ECs with 1) VEGF-A alone, IL-6 alone, or VEGF-A plus anti-IL-6 mAb, or with 2) IL-6 alone or IL-6 plus C3aR-A/C5aR-A, and assayed cell growth. Growth induction by IL-6 induced EC growth comparably to VEGF-A and VEGF-A's growth induction was abolished by anti-IL-6 (FIG. 27). The growth induction of ECs of IL-6, like that of VEGF-A, was abolished by C3aR-A/C5aR-A (FIG. 28). Both VEGF-A and IL-6 induced Stat3 phosphorylation and the Stat3 phosphorylation in both cases was abolished by C3aR/C5aR antagonism (FIG. 29). VEGF-A treatment or WT aortic ECs upregulated C3/C5 and increased local C3a/C5a generation as found in FIGS. 11-12 for MS-1 ECs, but neither change occurred in the presence of anti-IL-6 mAb or the JAK1 inhibitor (data not shown). These finding thus indicate that VEGF interconnects with C3aR/C5aR signaling via the induction of IL-6 and its activation of Stat3.

The data show that targeting C3aR and C5aR can repress pre cancer or cancer associated angiogenesis. Based on the data in this study mechanistically connecting C3aR/C5aR signaling with VEGFR2 signaling, such targeting should have value in other conditions including diabetic retinopathy rheumatoid arthritis (RA) where it has been shown that hypoxia and consequent angiogenesis augments the proliferation of synovial fibroblasts, systemic sclerosis where it has been shown that VEGF induced EC growth contributes to uncontrolled fibroblast growth and external ear canal cholesteatoma (EACC), an invasive and destructive external otitis, where it has been shown that migration of keritinocytes into the external ear is connected with increased expression of VEGF in all layers of the EACC-epithelium.

Example 2

Inflammatory cell influx and vascular cell proliferation underlie atherosclerotic progression and set the stage for thrombosis which eventuates in myocardial infarction and stroke. While many cell surface molecules and inflammatory mediators have been implicated in this self perpetuating process, the mechanisms that drive inflammation and proliferation remain incompletely characterized. We have found that both smooth muscle cells (SMCs) and monocytes/macrophages (mΦs) locally produce C3a and C5a activation fragments and that these anaphylatoxins interact with upregulated C3a and C5a receptors (C3aR and C5aR) on SMCs/mΦs. Our studies show that amplification of this signal transduction is what drives SMC/mΦ proliferation and evokes mΦs inflammatory cytokine production. This insight derived from our studies of immune cell activation which uncovered the previously unrecognized fact that local complement synthesis by interacting dendritic cells (DCs)- and T cells is an early event in T cell activation and that the resulting C3a/C5a-C3aR/C5aR interactions play a requisite role in T cell proliferation and effector cytokine, e.g., IFN-γ/IL-17 production. These studies in immune cells further showed that C3aR/C5aR signaling operates tonically to maintain T cell viability and suppress costimulatory molecule and innate cytokine, e.g., IL-1β/IL-12/IL-23 production. Importantly, our studies in SMCs/mΦs show that C3aR/C5aR signal transduction functions tonically similarly to that in immune cells. Our work has shown that the generation of C3a/C5a from locally synthesized complement by SMCs/mΦs, like that from immune cells, is regulated by the cell surface C3/C5 convertase inhibitor DAF and our studies now show that DAF expression is controlled by Kruppel-like factor 4 (KLF4). We have found that C3aR/C5aR signaling drives the neointimal response to endothelial cell (EC) injury. Our preliminary studies show that the mechanism underlying this is that amplified C3aR/C5aR signal transduction is essential for growth induction by platelet derived growth factor (PDGF), a factor important in both the EC response to injury and atherogenesis. In this Example, we 1) further characterized the interconnections of C3aR/C5aR signal transduction with platelet, leukocyte, EC, and SMC responses to EC injury, and found 2) the connections of C3aR/C5aR signal transduction with atherogenesis and thrombosis.

We found most cell types locally synthesize complement, and this local complement synthesis controls many cellular responses. Of particular interest, are findings documenting the local generation of C3a/C5a and the interaction of these fragments with C3aR/C5aR on endothelial cells (ECs), smooth muscle cells (SMCs), as well as myeloid cells, all of which are relevant to atherogenesis and possibly to its thrombotic sequelae. Local synthesis and activation in an autocrine fashion sustains EC/SMC viability and alters cellular production of and/or response to growth factors and cytokines. Importantly, this signaling loop is regulated by the cell surface C3/C5 convertase inhibitor, decay accelerating factor (DAF or CD55). Downregulation of DAF potentiates while upregulation suppresses C3aR/C5aR signaling and attendant effects on cellular viability and activation.

We found that vascular inflammation and neointimal formation are potentiated in mice deficient in Daf1 (the murine homolog of the human DAF gene), but completely attenuated in $Daf1^{-/-}C3aR^{-/-}$ and $Daf1^{-/-}C5aR^{-/-}$ mice. Data indicate that hypoxia and proinflammatory cytokines upregulate local EC complement production and local C3a/C5a generation, promoting leukocyte recruitment and activation. Finally, we have found that DAF expression is regulated by Kruppel like factor 4 (KLF4) in both ECs and immune cells. Based on these newly uncovered interconnections of autocrine C3aR/C5aR signaling in ECs, SMCs, and leukocytes, we show that local complement synthesis and autocrine C3aR/C5aR signaling regulates vascular cell responses to injury, which in turn contributes the development of atherosclerosis and thrombosis.

We found that autocrine/paracrine C3aR/C5aR signaling in ECs/monocytes/mΦs/SMCs is mechanistically linked to key proliferative and inflammatory processes that underlie the neointimal response of ECs to injury and participate in atherosclerotic progression to thrombosis. Evidence below implicates local C3aR/C5aR signaling in vascular proliferation, inflammation, injury, and repair.

PDGF contributes to atherogenesis and plays a central role in neointimal proliferation following EC injury. In view of the growth difference of primary cultured $Daf1^{-/-}$, WT, $C3aR^{-/-}C5aR^{-/-}$, and $C3^{-/-}C5^{-/-}$ SMCs, we examined whether C3aR/C5aR signals are interconnected with PDGF growth induction. For these studies, we utilized NIH-3T3 fibroblasts (which express PDGFR-αα) in conjunction with PDGF-AA. Following determination of optimal PDGF-AA doses, we incubated $1\times10^5$ cells/well in triplicate with 30 ng/ml of PDGF-AA±10 ng/ml of C3aR and C5aR antagonists (C3aR-A/C5aR-A), 10 ng/ml of anti-C3a/anti-C5a mAbs or respective controls, after which we quantified cell growth by counting cell numbers over time. Remarkably, blockade of either the receptors or their C3a/C5a ligands near completely suppressed PDGF-AA induced proliferation (FIG. 30A). Consistent with specificity, the growth of CTLL cells which is IL-2 dependent was not affected by C3aR/C5aR antagonism (FIG. 30B) and that of NIH-3T3 cells in 10% plasma was only partially inhibited. To directly establish whether C5aR signals augment PDGF-AA growth signaling, we 1) quantified the effect of added C5a one growth, and 2) assayed C5a in culture supernatants of PDGF-AA treated cells. This showed that a) added C5a (FIG. 31A) by itself induced proliferation, b) NIH-3T3 cells tonically produce C5a, and c) C5a generation by NIH-3T3 cells is amplified by PDGF-AA (FIG. 31B). Because the dependence of PDGF growth induction on C3aR/C5aR signaling could be indirect, i.e., a consequence of its requirement for viability, we performed cell cycle assays. Adding C5a to serum starved NIH-3T3 cells caused transition from G0 into G2 identically to adding PDGF indicating that autocrine C3aR/C5aR signals not only prevent apoptosis but drive growth.

To validate that these findings apply physiologically, we repeated the PDGF studies with the primary cultures of SMCs from aortas of WT, $Daf1^{-/-}$, and $C3aR^{-/-}C5aR^{-/-}$ mice. $Daf1^{-/-}$ SMCs (in which C3aR/C5aR signaling is potentiated) showed greater proliferation than WT SMCs in response to PDGF-AA, and $C3aR^{-/-}C5aR^{-/-}$ SMCs showed reduced proliferation. These findings show that C3aR/C5aR signal transduction in SMCs is important to their proliferative response in EC injury and atherogenesis. Results below show that a) atherogenesis is accelerated in the absence of DAF and b) the neointimal response to wire injury is markedly heightened in $Daf1^{-/-}$ mice but suppressed below that in WTs in $Daf1^{-/-}C3aR^{-/-}$ and $Daf1^{-/-}C5aR^{-/-}$ mice are consistent with this interpretation.

Antagonizing C3aR/C5aR signal transduction induces the synthesis and activation of TGF-β1. We investigated whether TGF-β1 production might underlie the growth suppression connected with C3aR/C5aR blockade. To test this, 1) we assayed supernatants from NIH-3T3 cells treated with PDGF-AA+anti-C3a/anti-C5a mAbs and 2) following removal of anti-C3a/anti-C5a from the mAb treated NIH-3T3 cell cultures (with protein-G beads), we added supernatants without or with anti-TGF-β1 blocking antibody to fresh cultures of PDGF-AA treated NIH-3T3 cells. These analyses showed that antagonizing C3aR/C5aR signaling induced active TGF-β1 expression (+2.5 ng/ml) and that the elicited TGF-β1 suppressed PDGF-AA induced growth (5-fold). RT-PCR of PDGF-AA treated NIH-3T3 cells showed that PDGF-AA suppressed TGF-β1 mRNA transcription (~3-fold), whereas C3aR/C5aR antagonism induced it. Activation of latent TGF-β1 can be dependent on Thrombospondin 1 (Tsp-1). Addition of anti-Tsp-1 Ab blocked the generation of active TGF-β1, indicating that Tsp-1 induction is also dependent on C3aR/C5aR antagonism (a result relevant to the pro-atherogenic phenotype of Tsp-1$^{-/-}$ mice). Collectively, these findings indicate that 1) disruption of C3aR/C5aR signaling evokes TGF-β1 production, 2) TGF-β1 enters into an autocrine signaling loop, and 3) C3aR/C5aR signals and TGF-β1 signals oppose each other in regulating PDGF induced growth.

ECs and leukocytes locally synthesize C3/fB/fD/C5 and the elicited C3a/C5a signal through C3aR/C5aR on the same cells to amplify this synthesis. To determine whether ECs locally synthesize AP complement components, we added IL-1/IFN-γ/TNF-α to HUVEC, 1 hr after which we quantified C3 and fB transcripts by qPCR. This analysis (FIG. 33A) showed marked upregulation of both mRNAs. Consistent with the ability of C3a/C5a to feed back through C3aR/C5aR and initiate an auto-inductive signaling loop, added C3a or C5a caused the ECs to make more AP components (FIGS. 33B-C). Incubation of HUVEC with the mitochondrial uncoupler protonophore carbonyl cyanide p-(trifluoromethoxy)phenylhydrazone (FCCP)+iodoacetate (IAA) (which simulate hypoxia when added to cells) also increased HUVEC complement synthesis (FIG. 33D). To test whether leukocytes that are recruited to sites of EC injury locally synthesize AP components and C5a similarly feeds back in them to amplify local complement production, we stimulated Raji, Jurkat, U937 cells, primary mΦs, B cells, and DCs with 10 nM C5a. This documented induction of AP and C5 gene transcription by qPCR.

DAF Attenuates Atherogenesis

To determine whether DAF's inhibition of C3/C5 activation retards atherogenesis, we crossed Daf1$^{-/-}$ mice with ApoE$^{-/-}$ or ldlr$^{-/-}$ mice, the two strains widely used to assess experimental atherosclerosis following high fat feeding. After placing homozygous Daf1$^{-/-}$ ApoE$^{-/-}$ and Daf1$^{-/-}$ ldlr$^{-/-}$ and their respective Daf1$^{+/+}$ littermates on a high fat diet to accelerate atherogenesis, we initially compared their coronary arteries and aortas for plaques at wk 11. On both backgrounds, immunohistochemical analyses showed 1.5-2-fold larger plaques (μ2/section), Moreover, there was more C3b deposition in DAF's absence. In a second cohort, we quantified lipid accumulation by Oil Red-O staining after 17 weeks of a high fat diet. Both gross and histologic analyses (FIG. 34) revealed a robust increase in atherosclerotic burden in Daf1-null animals.

In view of the connections of MCP-1 and other proinflammatory cytokines with atherosclerosis and the mechanistic linkage of DAF deficiency with potentiated C3aR/C5aR transduction, we tested whether C5aR signaling induces proinflammatory gene transcription. Added C5a induced the mRNA transcription of chemotactic MCP-1/IL-8, proinflammatory IL-1β/IL-6 and growth inductive GM-CSF.

DAF Regulates the Biological Response to EC Injury

Figure 35:
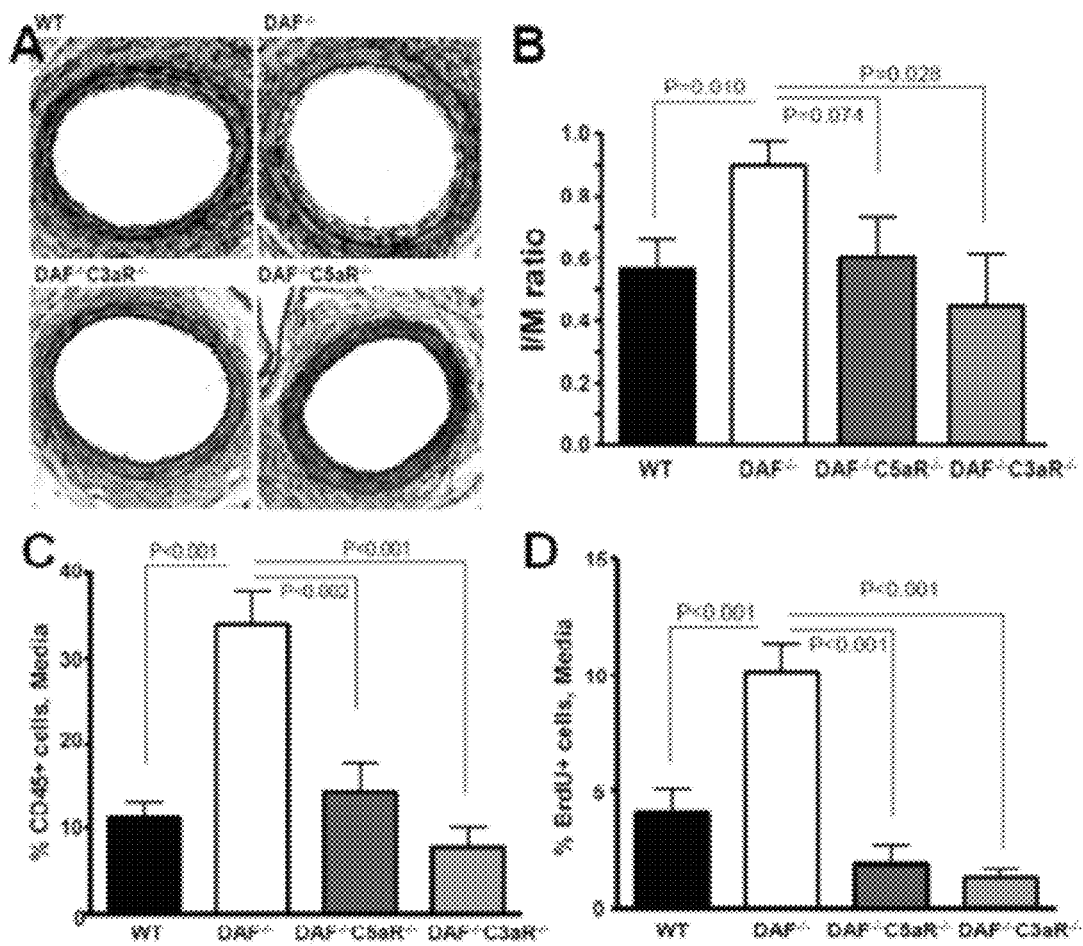
FIG. 35 illustrates images and charts showing: A) Verhoeffelastin stain 14 day after femoral artery wire injury (original magnification 10×). B) Intima area:media area ratio 14 d after injury. C) Medical Leukocyte (% CD45-positive cells) accumulation 14 d after injury. D) Cellular proliferation (% BrdU-positive cells) in the media 14 day after injury.

To directly test whether DAF regulates inflammatory and proliferative responses to EC injury, we compared femoral artery wire injury in Daf1$^{-/-}$ mice and WT controls. In this model, wire injury is accompanied by EC denudation, platelet and fibrin deposition, and prominent vascular inflammation. This model is used to closely mimic restenosis as seen following angioplasty in human patients. In WTs, we found that intimal thickening was evident 5 days post injury and further progressed between 5 and 14 days. Remarkably in Daf1$^{-/-}$ mice, at day 14, intimal thickening was 155% greater (p=0.026) (FIG. 35A) and the intima: media area ratio (I:M) was ~2-fold increased (0.90±0.20 vs. 0.57±0.41; p=0.01) compared to WT mice Immunohistochemical staining for C3dg, a C3b fragment, was significantly increased in Daf1$^{-/-}$ vs WT vessels (51.1±8.3% vs 30.6±10.0%; p=0.008; data not shown; FIG. 35B). In addition, Daf1$^{-/-}$ vessels exhibited increased immune cell infiltration (CD45+ staining; FIG. 35C) and cellular proliferation (BrdU staining; FIG. 35D). These studies identify a direct role for DAF in the proliferative and inflammatory response to mechanical vascular injury. To establish whether the mechanism by which its deficiency alters the vascular response to EC injury is increased by C3aR and/or C5aR signaling, we repeated the studies in Daf1$^{-/-}$C5aR$^{-/-}$ and Daf1$^{-/-}$C3aR$^{-/-}$ mice. We found that the augmented vascular inflammation, cellular proliferation, and neointimal thickening observed in Daf1$^{-/-}$ mice decreased to, or even below, WT levels in each KO animal (FIG. 35). In summary, the results demonstrated that DAF control of C3a/C5a generation and consequent C3aR/C5aR signaling is critical for the biological response to EC injury. These finding were recently confirmed in studies employing C3aR/C5aR antagonists.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, We claim:

1. A method of inhibiting platelet derived growth factor (PDGF) signaling of cells expressing C3a receptor (C3aR) and C5a receptor (C5aR) and PDGF receptor (PDGFR) of vasculature of a subject having or at risk of atherogenesis, the method comprising:

administering to the cells of the vasculature of the subject at a site proximate or about the periphery of a vascular injury a therapeutically effective amount of an antibody directed against C3aR that inhibits C3a interaction with C3aR and an antibody against C5aR that inhibits C5a interaction with C5aR to inhibit C3aR and C5aR signaling of the cells and treat atherogenesis in the subject.

2. The method of claim 1, the cells comprising at least one of smooth muscle cells or endothelial cells of the vasculature.

3. The method of claim 2, the antibody directed against C3aR and the antibody against C5aR being administered to the subject to inhibit at least one of growth, viability, or mitosis of the cells following PDGF stimulation of the cells.

4. A method of inhibiting platelet derived growth factor (PDGF) signaling of cells expressing C3a receptor (C3aR) and C5a receptor (C5aR) and PDGF receptor (PDGFR) of vasculature of a subject having or at risk of atherogenesis, the method comprising:

administering to the cells of the vasculature of the subject at a site proximate or about the periphery of a vascular injury a therapeutically effective amounts of a C3a or C3aR antagonist and a C5a or C5aR antagonist to inhibit C3aR and C5aR signaling of the cells and treats atherogenesis in the subject, the C3a or C3aR antagonist and the C5a or C5aR antagonist substantially reduce the interaction of C3a with the C3a receptor (C3aR) and C5a with the C5a receptor (C5aR).

5. The method of claim 4, the cells comprising at least one of smooth muscle cells or endothelial cells of the vasculature.

6. The method of claim 5, the C3a or C3aR antagonist and the C5a or C5aR antagonist being administered to the subject to inhibit at least one of growth, viability, or mitosis of the cells following PDGF stimulation of the cells.

7. The method of claim 4, the C3aR antagonist comprising an antibody directed against C3aR that inhibits C3a interaction with C3aR and the C5aR antagonist comprising an antibody against C5aR that inhibits C5a interaction with C5aR.

* * * * *